US011672873B1

United States Patent
Schilling et al.

(10) Patent No.: US 11,672,873 B1
(45) Date of Patent: *Jun. 13, 2023

(54) ANTI-B7-H4 ANTIBODIES AND METHODS

(71) Applicant: NantBio, Inc., Culver City, CA (US)

(72) Inventors: Benjamin Schilling, Culver City, CA (US); C. Anders Olson, Culver City, CA (US); Philip T. Liu, Culver City, CA (US); Shiho Tanaka, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 289 days.

This patent is subject to a terminal disclaimer.

(21) Appl. No.: 17/027,564

(22) Filed: Sep. 21, 2020

Related U.S. Application Data

(63) Continuation of application No. 16/010,334, filed on Jun. 15, 2018, now Pat. No. 10,814,011.

(60) Provisional application No. 62/521,124, filed on Jun. 16, 2017.

(51) Int. Cl.
| | | |
|---|---|---|
| *A61K 47/68* | (2017.01) |
| *A61P 35/00* | (2006.01) |
| *A61K 39/00* | (2006.01) |
| *C07K 16/24* | (2006.01) |
| *A61K 39/395* | (2006.01) |

(52) U.S. Cl.
CPC .......... *A61K 47/6879* (2017.08); *A61K 39/00* (2013.01); *A61K 39/395* (2013.01); *A61K 47/6801* (2017.08); *A61K 47/6849* (2017.08); *A61K 47/6851* (2017.08); *A61P 35/00* (2018.01); *C07K 16/244* (2013.01)

(58) Field of Classification Search
None
See application file for complete search history.

(56) References Cited

U.S. PATENT DOCUMENTS

| 9,562,099 B2 | 2/2017 | Leong et al. |
| 9,574,000 B2 | 2/2017 | Langermann et al. |
| 10,814,011 B1 * | 10/2020 | Schilling .............. C07K 16/244 |

FOREIGN PATENT DOCUMENTS

WO 2016/160620 A2 10/2016

OTHER PUBLICATIONS

Zhang et al. 'B7-H1 protein vaccine induces protective and therapeutic antitumor responses in SP2/0 myeloma-bearing mice.' Oncology Reports 30:2442-2448, 2013.*
Anti-B7H4 antibody [H74] (Alpha110160), http://www.abcam.com/b7h4antibodyh74ab110160.ntml, May 22, 2017, 4 pages.
APC anti-human B7-H4 Antibody, www.biolegend.com, May 5, 2005, 3 pages.
Dangaj et al., "Novel Recombinant Human B7-H4 Antibodies Overcome Tumoral Immune Escape to Potentiate T-Cell Anti tumor Responses", Cancer research, 2013, vol. 73, No. 15, pp. 4820-4829.
Smith et al., "B7-H4 as a potential target for immunotherapy for gynecologic cancers: A closer look", NIH Public Access, Gynecol Oncol, Jul. 2014, vol. 134, No. 1, 20 pages.
Sica et al., "B7-H4, a Molecule of the B7 Family, Negatively Regulates T Cell Immunity", Immunity, vol. 18, Jun. 2003, pp. 849-861.
Miariuzza et al., "The Structural Basis of Antigen-Antibody Recognition", Annu. Rev. Biophys. Biphys. Chem., 1987, vol. 16, pp. 139-159.
Felices et al., "Generation of BiKEs and TriKEs to improve NK cell-mediated targeting of tumor cells", Methods Mol Biol., 2016, vol. 1441, 15 pages (doi: 10.1007/978-1-4939-3684-7 28).
Goel et al., "Plasticity within the Antigen-Combining Site May Manifest as Molecular Mimicry in the Humoral Immune Response", The Journal of Immunology, 2004, vol. 173, No. 12, pp. 7358-7367.
Kahn et al. Adjustable Locks and Flexible Keys: Plasticity of Epitope-Paratope Interactions in Germline Antibodies, The Journal of Immunology, 2014, vol. 192, pp. 5398-5405. Poosarla et al., "Computational De Novo Design of Antibodies Binding to a Peptide With High Affinity", Biotechnology Bioengineering, 2017, vol. 114, No. 6, pp. 1331-1342.
MacCallum et al., "Antibody-antigen interactions: contact analysis and binding site topography", J. Mol. Biol., 1996, vol. 262, pp. 732-745.

(Continued)

*Primary Examiner* — Nora M Rooney
(74) *Attorney, Agent, or Firm* — Martin Fessenmaier; Umberg Zipser LLP

(57) ABSTRACT

Compositions, methods, and uses of recombinant B7-H4 protein or binding motifs to B7-H4 protein that can reduce the immune suppression effect of B7-H4 in relation to T cell activation, proliferation, and conversion. Preferably, the recombinant B7-H4 protein has a plurality of mutations in N-glycosylation residue to reduce its inhibitory effect to T cell activation and proliferation. The recombinant protein having binding motifs to B7-H4 protein preferably includes a binding motif to IgC domain and another binding motif to IgV domain such that the immune-suppressive effects by two Ig-like domains are concurrently reduced.

20 Claims, 25 Drawing Sheets

Specification includes a Sequence Listing.

(56) References Cited

OTHER PUBLICATIONS

De Pascalis et al., "Grafting of abbreviated complementarity-determining regions containing specificity-determining residues essential for ligand contact to engineer a less immunogenic humanzied monoclonal antibody", The Journal of Immunology, 2002, vol. 169, pp. 3076-3084.
Barendt et al., "Streamlined Protocol for mRNA Display", ACS Combinational Science, 2013, vol. 15, No. 2, pp. 77-81.
Non Final Office Action received for U.S. Appl. No. 16/010,334 dated Apr. 1, 2020, 22 pages.
Notice of Allowance received for U.S. Appl. No. 16/010,334 dated Aug. 5, 2020, 15 pages.

* cited by examiner

ANTI-B7-H4 ANTIBODIES AND METHODS

This application is a continuation application of our currently allowed U.S. application with the Ser. No. 16/010,334, filed Jun. 15, 2018, which claims priority to U.S. provisional application with Ser. No. 62/521,124, filed Jun. 16, 2017.

FIELD OF THE INVENTION

The field of the invention is compositions and methods related to native and mutant forms of B7-H4, and to antibodies and portions thereof that bind to B7-H4.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Peripheral tolerance is a crucial process that maintains the immune homeostasis and prevents defective immune reaction. The key controlling mechanism responsible for the peripheral tolerance is the requirement for two independent signals during the initial priming of naïve T cells by the professional antigen presenting cells (APC). Signal one is antigen-specific. It is delivered through binding of the T cell receptor (TCR) to its antigenic peptide loaded onto major histocompatibility complex class II (MHC II) molecules. The second signal is co-stimulatory. It is conveyed by the interaction of one or several co-stimulatory ligands on APCs' surface with the cognate receptors on T cells. T cell priming outcome correlates directly with the nature of the co-stimulatory signal. Positive co-stimulation results in activation of naïve T cells, while negative co-stimulation drives them into anergy. The B7 family of co-stimulatory ligands are well known molecules that impart stimulatory or inhibitory signaling to T cells.

As a member of the B7 family, B7-H4 (also known as V-set Domain-Containing T Cell Activation Inhibitor 1 (VTCN1), B7x and B7S1) is involved in the control of T cell activation. B7-H4 binds preferably to activated T cells ($CD4^+$ and $CD8^+$) inhibiting their proliferation and IL-2 cytokine production. Viewed from a structural perspective, B7-H4 is a member of the immunoglobulin (Ig) superfamily containing two Ig-like domains: a variable (IgV) and a constant (IgC) domain. Similar to another negative co-stimulators, PD-L1, B7-H4 is expressed not only by APCs but also in a variety of normal non-lymphoid and cancerous tissues. The expression by non-APCs implicates that B7-H4 might also have additional functions to the one of a classical co-stimulatory molecule. Multiple studies confirmed such a hypothesis linking the high B7-H4 expression by non-APC's with variety of carcinomas.

Tissue specific overexpression of B7-H4 was correlated with negative clinical outcomes in prostate cancer, ovarian cancer, breast cancer, pancreatic cancer, and renal cancer. Recently, the inventors showed that impaired B7-H4 presentation marks type I diabetes development in both mouse models and human patients, linking this process to a proteolytic shedding of cell surface B7-H4 from APCs and pancreatic islets. Ig treatment reduced the incidence of T1D, experimental autoimmune encephalomyelitis, and rheumatoid arthritis, highlighting its importance as a potential therapeutic target for both autoimmunity and cancer.

As an extracellular protein, B7-H4 is highly glycosylated. Glycosylation is the main post-translational modification of the extracellular proteins, crucial for maintaining protein stability, protein trafficking, receptor binding and protein folding. Impairment of multiple N-linked glycosylated proteins have been implemented in T cell mediated autoimmunity and various tumors. Previously, the heterogeneity in B7-H4 size observed in different tumor cells and tissues has been explained with the N-linked glycosylation, as tumor specific glycosylation pattern was speculated to manipulate B7-H4 interactions and functions, even though there was no direct evidence supporting such a conclusion as the B7-H4 receptor is still elusive. Hence, the impact of the glycosylation in B7-H4 co-stimulatory function is, therefore, yet to be revealed.

Regardless of the extensive research, the mechanism of B7-H4 action remains unknown. The crystal structure of its IgV-like domain showed conserved loops similar to the PD-L1 IgV-like domain suggesting that B7-H4 function relies on an IgV-mediated signaling pathway. Moreover, the use of IgV-specific antibodies alleviated the growth of B7-H4-expressing tumors in vivo. That is why the conclusion that IgV domain is the receptor-binding domain of B7-H4 was drawn. Generally, the IgV domain of the B7-family ligands is considered as the function-implementing domain, and the IgC domain is displayed as the one maintaining the integrity of the molecules, during receptor binding. However, the direct functional role of IgV and IgC domain of B7-H4 in T cell function has never been studied.

To that end, various compositions targeting B7-H4 have been developed and antibodies are commercially available (e.g., Biolegend Clone MIH43; Abcam ab 110160). Moreover, there are also various pharmaceutical compositions reported using antibodies and fragments thereof (see e.g., U.S. Pat. Nos. 9,562,099, 9,574,000). Furthermore, CAR T-cells were reported for the treatment of B7-H4 expressing tumors as disclosed in WO 2016/160620. However, while targeting B7-H4 is an at least conceptually attractive route, clinically effective compositions are currently not available. Moreover, antibodies against B7-H4 need relatively low $K_D$ and high specificity, and as such may present a significant obstacle.

Thus, even though various compositions and methods associated with B7-H4 are known in the art, various difficulties nevertheless remain. Therefore, there is still a need for improved therapeutic and/or diagnostic compositions and methods that make use of or target B7-H4 in vivo and/or in vitro with high specificity and affinity.

SUMMARY OF THE INVENTION

The inventive subject matter is directed to various compositions and methods of targeting B7-H4 using an antibody or fragment thereof, alone or in combination with one or more non-antibody portion (e.g., chimeric protein, cell, polymeric carrier, etc.). Further the inventive subject matter is directed to mitigating the B7-H4 effect on immune suppression in the tumor microenvironment by competitive antagonist of B7-H4.

Thus, in one aspect of the inventive subject matter, the inventors contemplate an isolated antibody or fragment thereof binding to B7-H4, and having at least one domain selected from the group consisting of $VH_{801}$, $VL_{801}$, $VH_{817}$, and $VL_{817}$.

In preferred embodiments, $VH_{801}$ comprises or has a sequence of EVQLVESGGGLVQPGGSLRLS-CAASGFTFNSYAMHWVRQAPGKGLEWVSAIS-GNGGST RYADSVKGRFTISRDNSKNTLYLQMNSL-RAEDTAVYYCARDRFRKVHGFDVWGQGTL VTVSS (SEQ ID NO:1), $VLg_{801}$ comprises or has a sequence of DIQMTQSPSSLSASVGDRVTITCQASQDIS-NYLNWYQQKPGKAPKLLIYDASNLETGVPS RFSGSGSGTDFTFTISSLQPEDIATYYCQQ-DATFPLTFGQGTKVEIK (SEQ ID NO:2), $VH_{817}$ comprises or has a sequence of EVQLVESGG-GLVQPGGSLRLSCAASGFTFSSYAMHWVRQAPGKGL EWVSAISGSGGST RYADSVKGRFTISRDNSKNT-LYLQMNSLRAEDTAVYYCAR-GRWSKWGFDVWGQGTL VTVSS (SEQ ID NO:3), and $VL_{817}$ comprises or has a sequence of DIQMTQSPSSL-SASVGDRVTITCQASQDIS-NYLNWYQQKPGKAPKLLIYDASNLETGVPS RFSGSGSGTDFTFTISSLQPEDIATYYCQQTDNFPY-TFGQGTKVEIK (SEQ ID NO:4).

Depending on the particular embodiments the antibody or fragment as presented herein may include $VH_{801}$ and $VL_{801}$, or $VH_{817}$ and $VL_{817}$, with VH and VL optionally coupled together by a linker to form an scFv. Alternatively, the antibody may be an $IgG_1$ antibody, and most preferably a human antibody. Of course, it should also be appreciated that any one of the CDRs in any one of $VH_{801}$ and $VL_{801}$, $VH_{817}$ and $VL_{817}$ may be grafted into a suitable antibody (fragment) scaffold.

Where desired, the antibody or fragment may further include a therapeutic agent, and especially contemplated therapeutic agents include a chemotherapeutic drug, a radionuclide, and/or an immune stimulant (e.g., a cytokine, a cytokine analog, a chemokine, or a checkpoint inhibitor). Moreover, contemplated antibodies or fragments thereof may also have a detectable label (e.g., an optically detectable label, an isotope label, or an affinity label, or the detectable label may comprise an enzyme). In further preferred aspects, the antibody or fragment will have a $K_D$ with respect to binding B7-H4 of equal or less than 500 pM, and more typically equal or less than 200 pM, and in some cases equal or less than 100 pM.

In still further contemplated aspects, the inventors also contemplate a chimeric protein that includes the antibody or fragment as presented herein. For example, the chimeric protein may be configured as a chimeric antigen receptor, which may preferably be expressed on an NK cell or a cytotoxic T cell. Alternatively, the chimeric protein may also be configured as a bispecific fusion protein, and particularly preferred bispecific fusion proteins include an IgG Fc portion, and optionally further at least one of an IL15a receptor portion, an IL15 portion, and an IL15 superagonist portion. Additionally, such fusion proteins may also comprise an anti-PD-L1 portion. Moreover, contemplated chimeric proteins may also be configured as a bispecific killer cell engager (BiKE) or a trispecific killer cell engager (TriKE).

Still another aspect of the inventive subject matter includes a pharmaceutical composition comprising an extracellular portion of a hypo-glycosylated mutant form of B7-H4. Generally, the hypo-glycosylated mutant form of B7-H4 has a mutation in a N-glycosylation residues in B7H4, wherein the N-glycosylation residues are selected from a group consisting of N112, N160, N190, N196, N205, N216 and N220. In a preferred embodiment, the hypo-glycosylated mutant form of B7H4 has mutations in at least three N-glycosylation residues in B7H4.

In still another aspect of the inventive subject matter, the inventors contemplate a recombinant expression vector for immune therapy that includes a nucleic acid sequence that encodes a hypo-glycosylated mutant form of B7-H4. Generally, the hypo-glycosylated mutant form of B7-H4 has a mutation in a N-glycosylation residues in B7H4, wherein the N-glycosylation residues are selected from a group consisting of N112, N160, N190, N196, N205, N216 and N220. In a preferred embodiment, the hypo-glycosylated mutant form of B7H4 has mutations in at least three N-glycosylation residues in B7H4. Preferably, the expression vector is selected from a group consisting of a viral expression vector, a bacteria expression vector, and a yeast expression vector.

Still another aspect of the inventive subject matter includes a method of increasing effectiveness of immune therapy in a patient having a tumor. In this method, a pharmaceutical composition comprising an extracellular portion of a hypo-glycosylated mutant form of B7-H4 is provided. Generally, the hypo-glycosylated mutant form of B7-H4 has a mutation in a N-glycosylation residues in B7H4, wherein the N-glycosylation residues are selected from a group consisting of N112, N160, N190, N196, N205, N216 and N220. In a preferred embodiment, the hypo-glycosylated mutant form of B7H4 has mutations in at least three N-glycosylation residues in B7H4. Then, the pharmaceutical composition is administered to the patient in a dose and schedule effective to reduce immune suppression in the patient.

In still another aspect of the inventive subject matter, the inventors contemplate a method of increasing effectiveness of immune therapy in a patient having a tumor. In this method, a cancer vaccine comprising a nucleic acid sequence that encodes a hypo-glycosylated mutant form of B7-H4 is provided. Generally, the hypo-glycosylated mutant form of B7-H4 has a mutation in N-glycosylation residues in B7H4, wherein the N-glycosylation residues are selected from a group consisting of N112, N160, N190, N196, N205, N216 and N220. In a preferred embodiment, the hypo-glycosylated mutant form of B7H4 has mutations in at least three N-glycosylation residues in B7H4. Preferably, the expression vector is selected from a group consisting of a viral expression vector, a bacteria expression vector, and a yeast expression vector. Then, the cancer vaccine is administered to the patient in a dose and schedule effective to reduce immune suppression in the patient.

Still another aspect of the inventive subject matter includes a recombinant protein complex that includes a first binding motif to IgC portion of B7H4 and a second binding motif to IgV portion of B7H4. Where desired, the first and second binding motifs can concurrently bind to a single B7H4 molecule. In other embodiments, the first and second binding motifs are coupled via a linker. In still other embodiments, at least one of the first and second binding motifs are coupled to a recombinant immunoglobulin protein complex, which is preferably an IL-15 superagonist.

In still another aspect of the inventive subject matter, the inventors contemplate a method of increasing effectiveness of immune therapy to a patient having a tumor, typically by reduction of immune suppression in the patient. In this method, a pharmaceutical composition comprising encoding recombinant protein complex that includes a first binding motif to IgC portion of B7H4, and a second binding motif to IgV portion of B7H4 is provided. Preferably, the first and second binding motifs can concurrently bind to a single B7H4 molecule. In some embodiments, the first and second binding motifs are coupled via a linker. In other embodiments, at least one of the first and second binding motifs are coupled to a recombinant immunoglobulin protein complex, which is preferably an IL-15 superagonist. Then, the pharmaceutical composition is administered to the patient in a dose and schedule effective to reduce immune suppression in the patient.

Still another aspect of the inventive subject matter includes use of a pharmaceutical composition, the expression vector, or the recombinant protein complex as described above the recombinant protein complex or for reducing the immune suppression in a tumor microenvironment in a patient having a tumor.

Various objects, features, aspects and advantages of the inventive subject matter will become more apparent from the following detailed description of preferred embodiments, along with the accompanying drawing figures in which like numerals represent like components.

Next, gated cells were analyzed either for proliferation or Treg population based on CD25 and FoxP3 positivity. (B) Gating strategy for identification of CD8+Tregs. Cells were gated similarly to (A). (C) Gating strategy for human CD4+Tregs. (D) Gating strategy for human CD8+Tregs.

Figure 15:
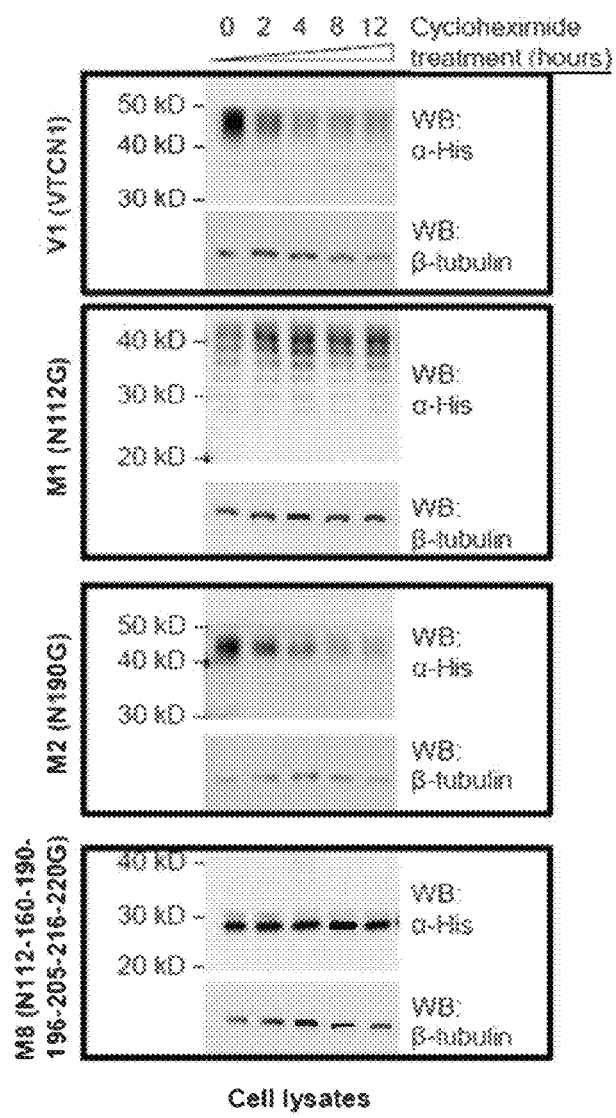

FIG. 15 shows western blots indicating turnover rate (half-life) of recombinant V1 constructs. Western blots of cell lysates from HEK cells that were transfected with the indicated recombinant protein.24 h post-transfection, the cells were incubated in the presence of cyclohexamide and aliquots were collected at different time points (0-12 hrs) for western blot analysis.

Figure 14:
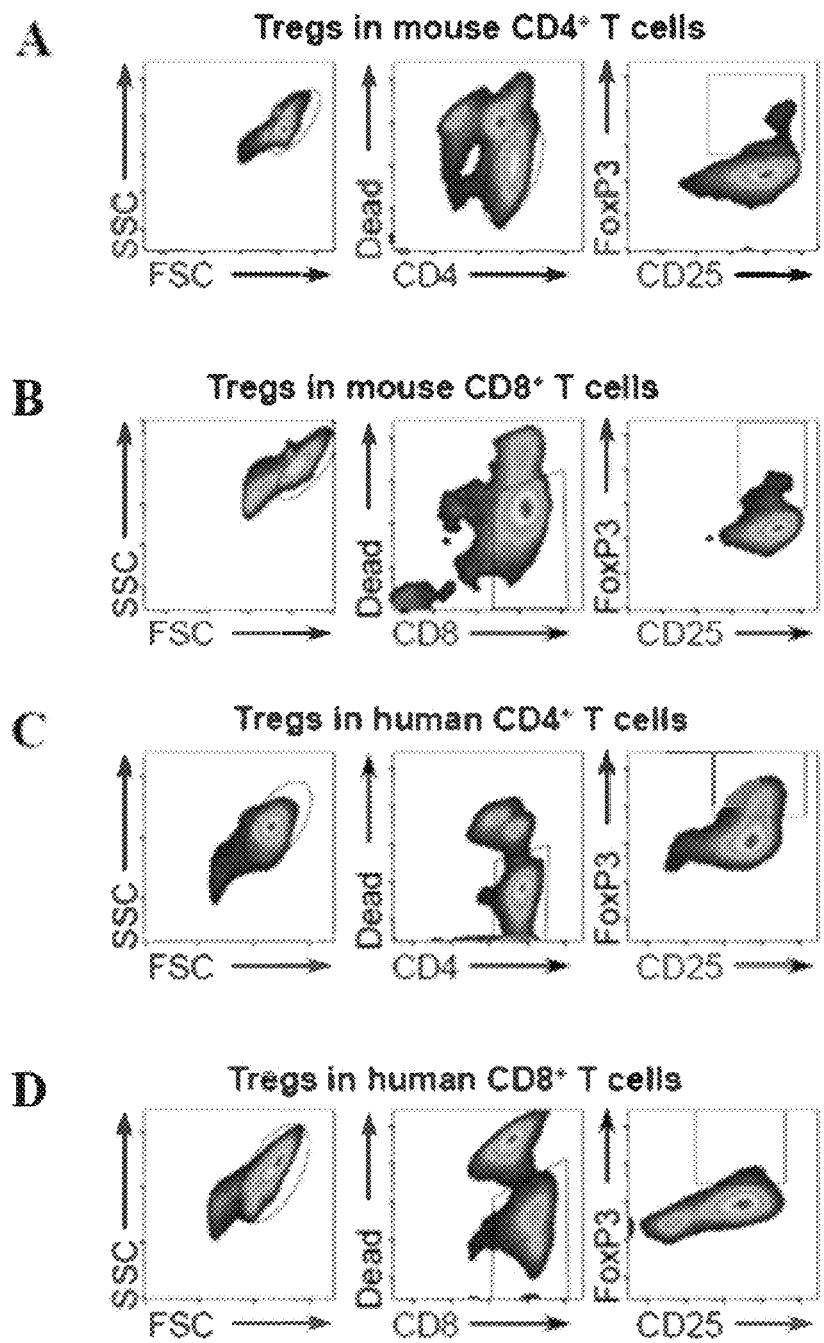
FIGS. 14 A-D depicts gating strategy and flow cytometric staining patterns. Gating strategy for identification of CD4+ Tregs.(A) Cells (excluding the beads in experiments where T cells were activated with anti CD3/CD28 Dyna beads) were gated, and live CD4+T cells were selected.
Figure 16:
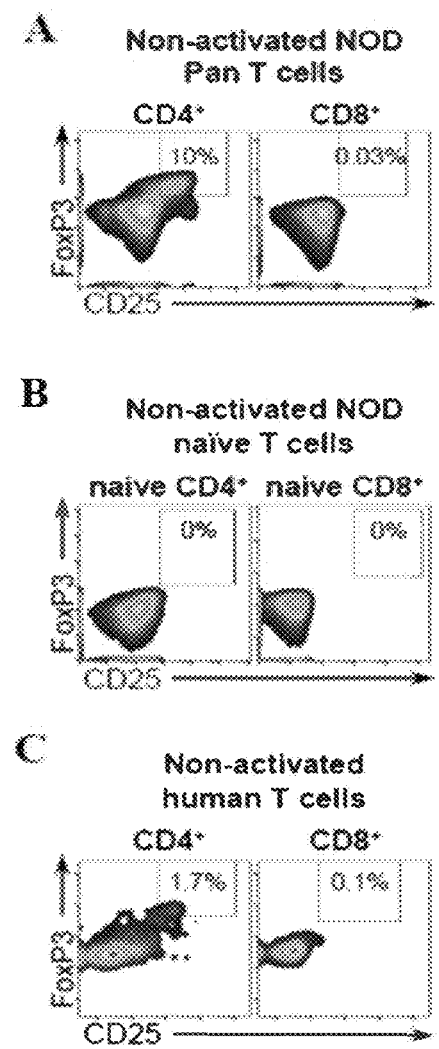

FIG. 16 shows FACS analysis presenting percentage of Tregs in various T cell populations. A) Tregs in freshly isolated NOD Pan T cells. Gating was performed as described on FIG. 14.B) Tregs in isolated murine naïve CD4+ and CD8+T cells. C) Tregs in non-activated human CD4+ and CD8+T cells purchased from Stem Cell Technologies.

Figure 17:
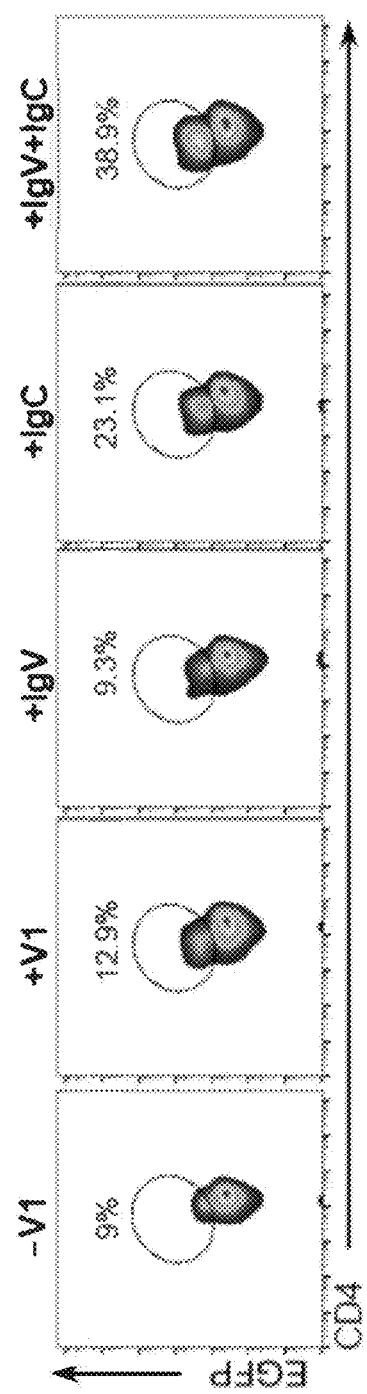

FIG. 17 shows FACS analysis presenting conversion of naïve CD4+T cells isolated from NOD-FOXP3. Naïve CD4+CD25−T cells were isolated from spleens of NOD-FOXP3. EGFP mice and then activated with anti-CD3/CD28 microbeads in the presence or absence of the indicated recombinant molecule. After 5 days of activation, cells were collected and analyzed for EGFP expression by FACS.

Figure 18:
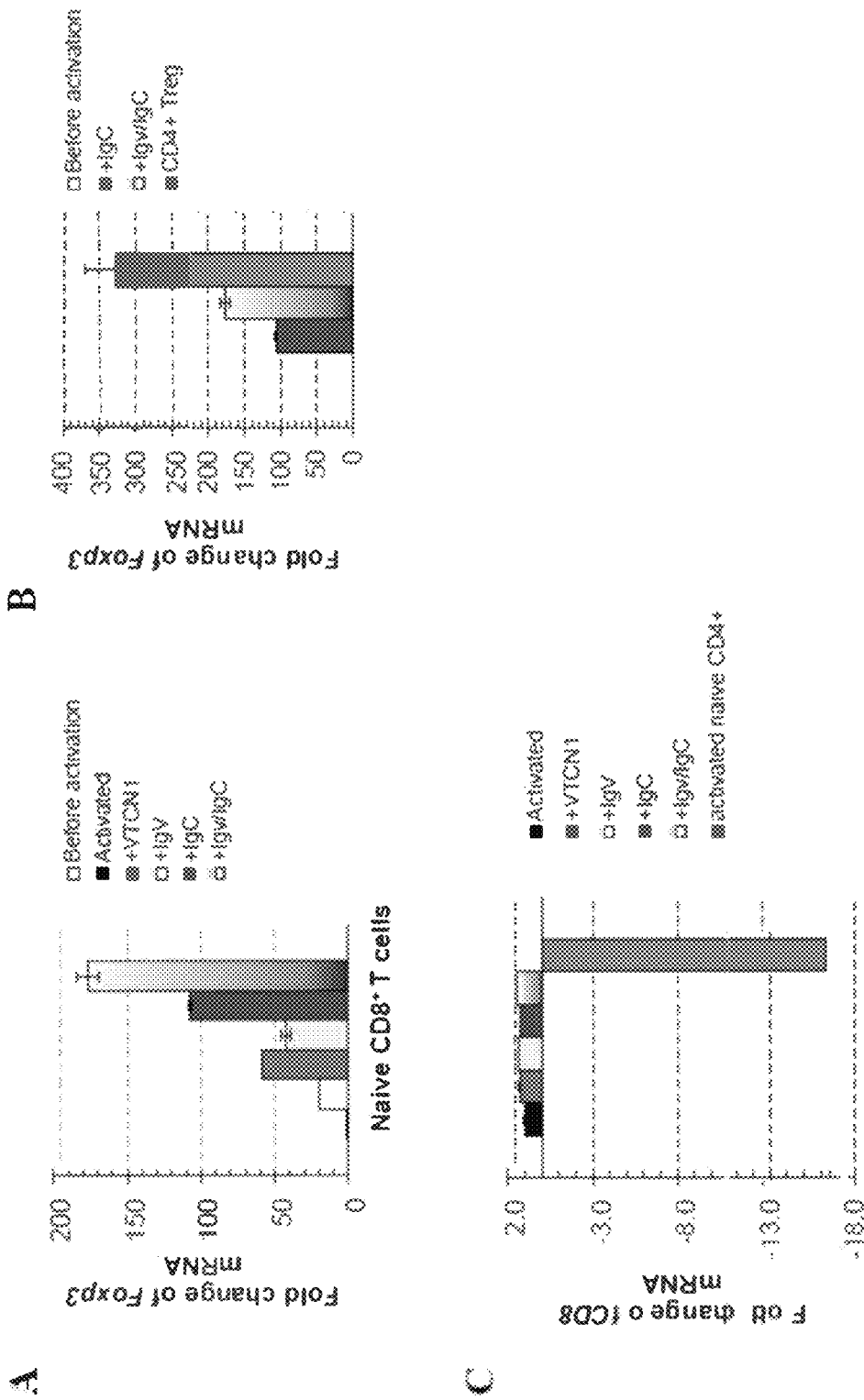

FIG. 18 shows bar graphs of expression levels of Foxp3 mRNA by treating various B7-H4 constructs. Naïve CD8+ CD25−T cells were activated with anti-CD3/CD28 microbeads in the presence or absence of the indicated recombinant protein. After 72 hours, cells were collected, total RNA was isolated and then used for RT qPCR. As a control, freshly isolated naïve CD8+T cells were used. (A) Changes in Foxp3 gene expression levels. (B) Comparison of Foxp3 expression levels in converted CD8+Tregs with freshly isolated classical CD4+Treg cells. (C) Comparison of the CD8 expression in activated naïve CD8+cells to activated naïve CD4+ cells.

Figure 19:
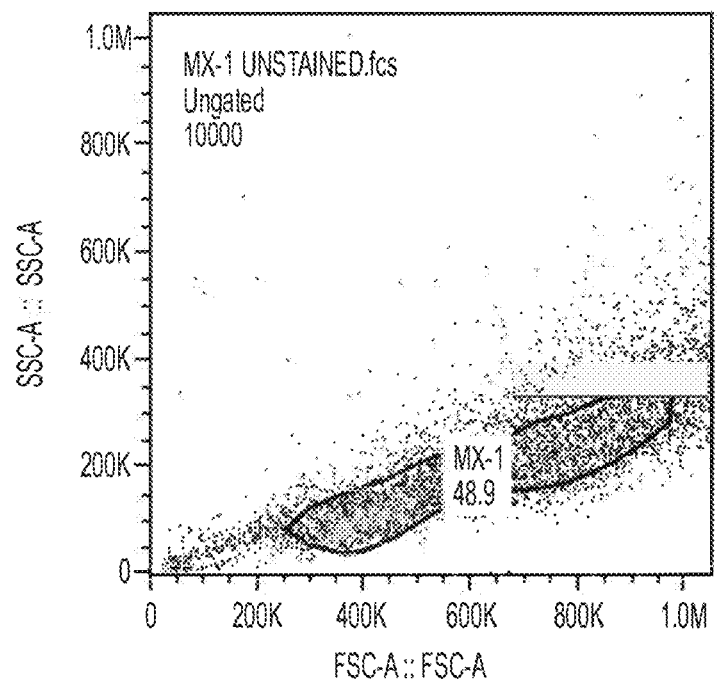
Figure 19:
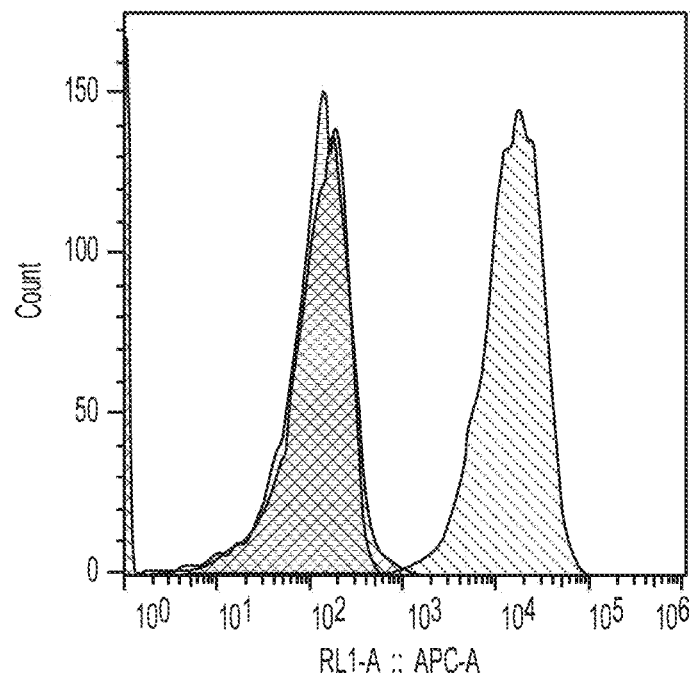
Figure 19:
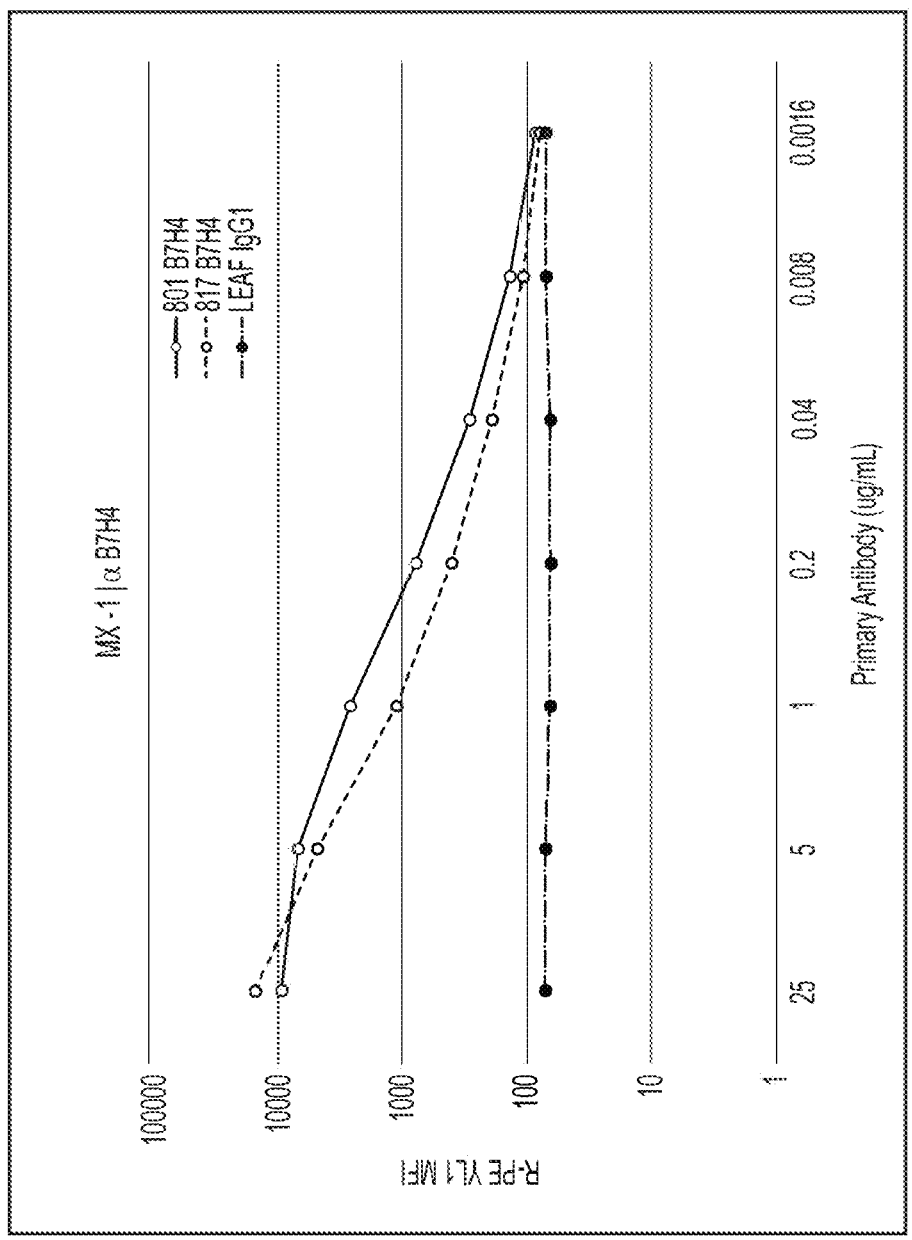

FIG. 19 depicts exemplary results of staining MX-1 with 801 and 817 antibodies, along with results establishing presence of B7-H4 on the cell surface.

Figure 20:
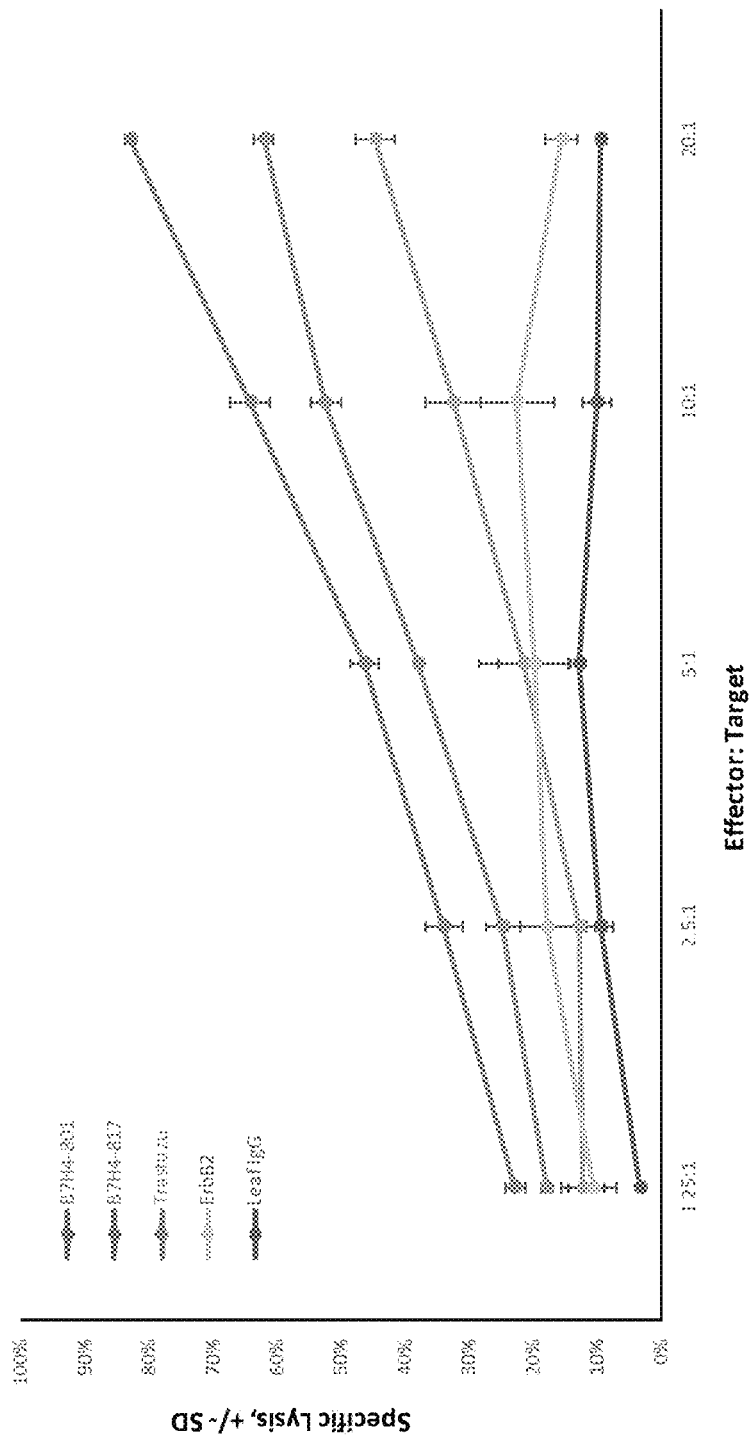

FIG. 20 depicts exemplary results of cytotoxicity of antiB7-H4 antibodies on MX-1 cells.

Figure 21:
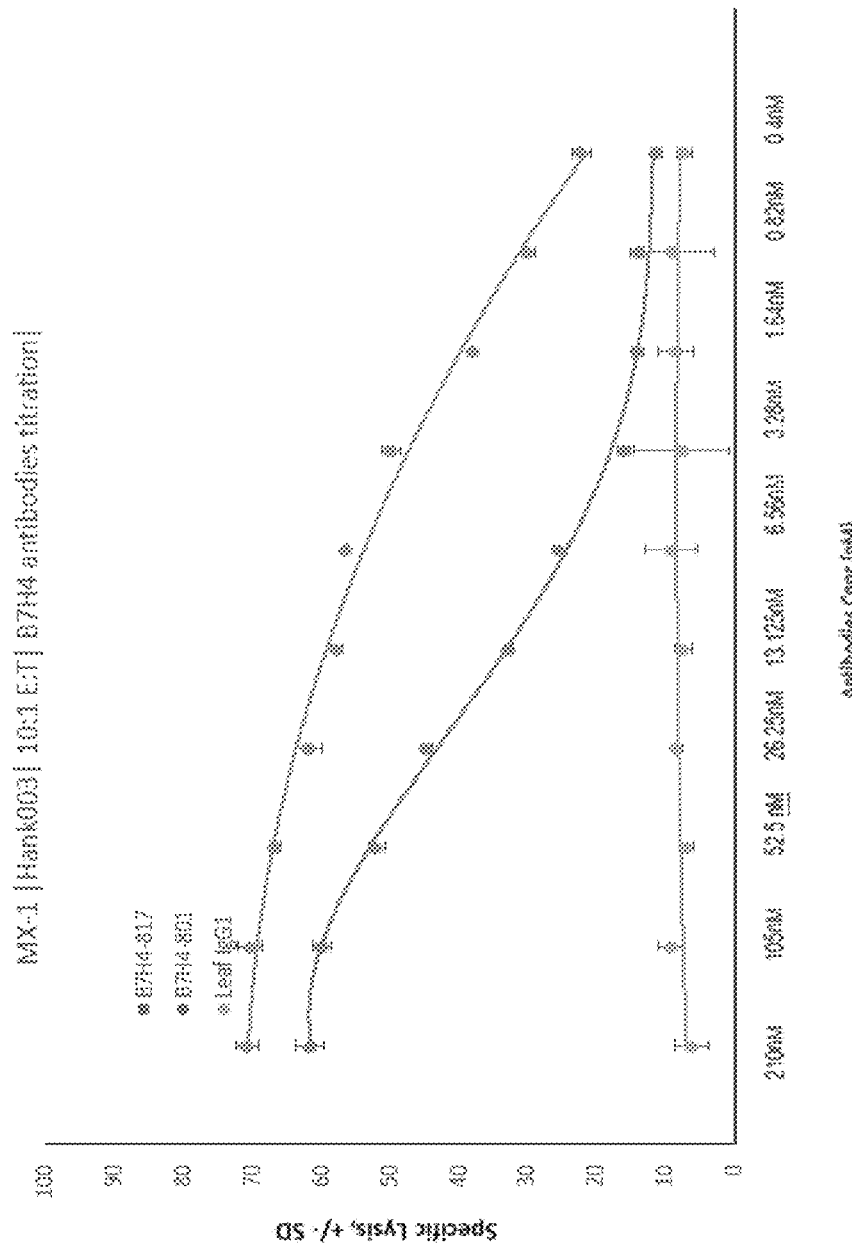

FIG. 21 depicts exemplary results of antiB7-H4 antibody-mediated haNK cell cytotoxicity on MX-1 cells.

Figure 22:
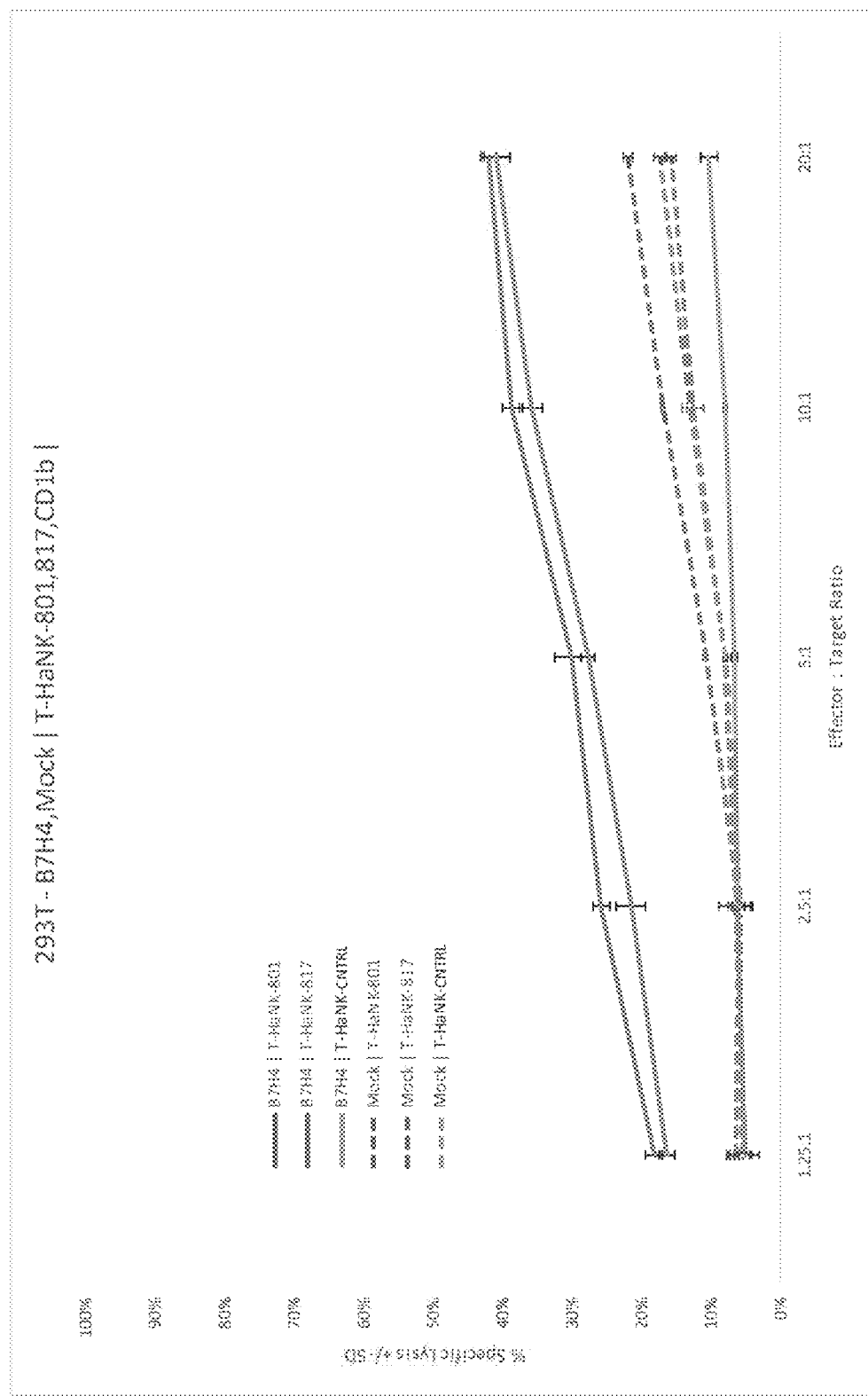

FIG. 22 depicts exemplary results of antiB7-H4 antibody-mediated haNK cell cytotoxicity on B7-H4 transfected 293T cells.

Figure 23:
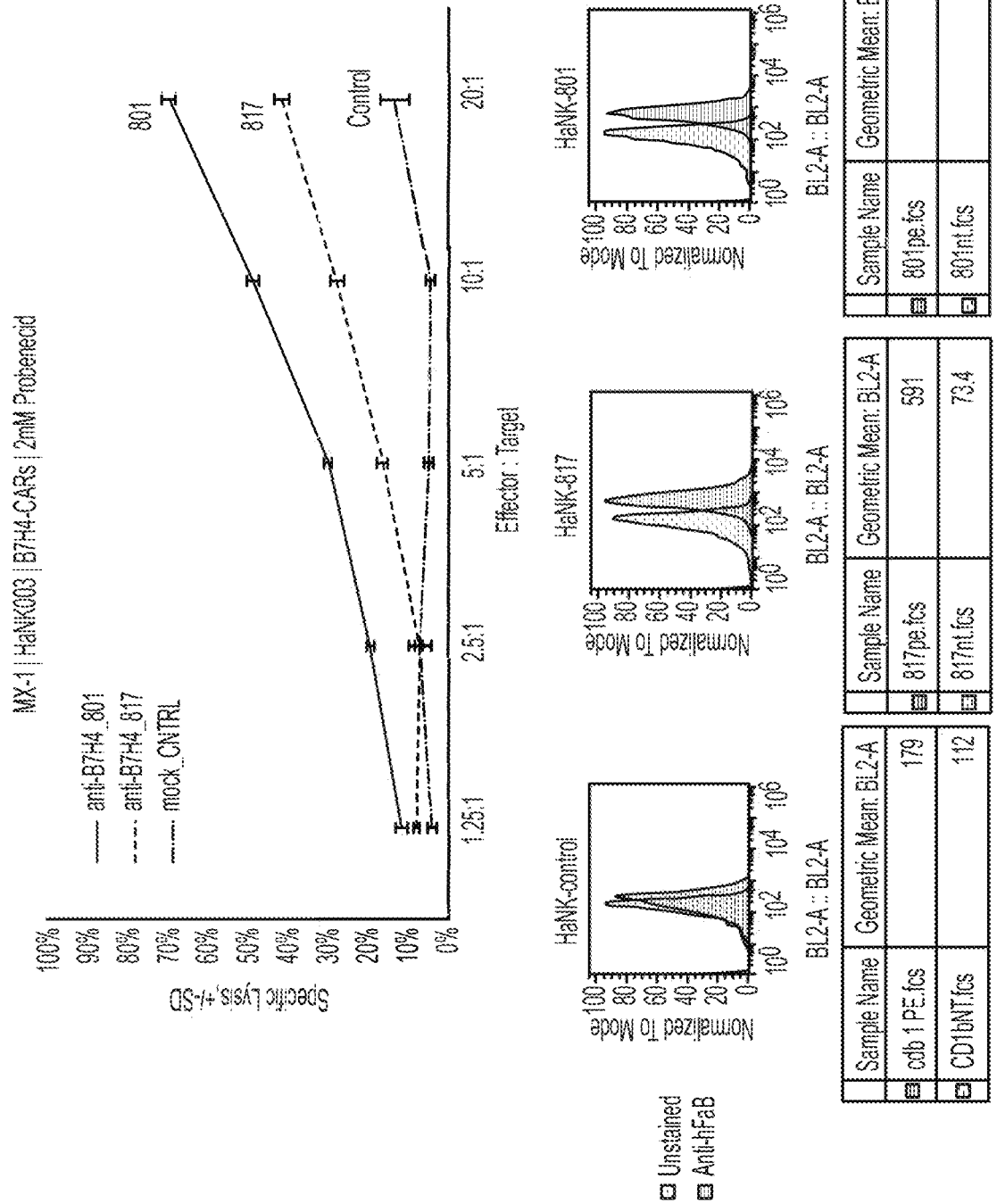

FIG. 23 depicts exemplary results of cytotoxicity for haNK cells expressing a CAR with an antiB7-H4 ectodomain.

DETAILED DESCRIPTION

The inventors have discovered various anti-B7-H4 antibodies that have high affinity and specificity with respect to binding of B7-H4 with. In particularly preferred aspects, contemplated antibodies are human IgG$_1$ antibodies that have the V$_H$ and V$_L$ sequences (or at least some of the CDRs (shown underlined) in any one of the sequences) as shown below.

More particularly, a first anti-B7-H4 antibody (801) has a V$_{H-801}$ sequence (SEQ ID NO: 1):
EVQLVESGGGLVQPGGSLRLSCAAS<u>GFTFNSY</u>AMHWVRQAPGKGLEWV
SAI<u>SGNGGS</u>TRYADSVKGRFTISRDNSKNTLYLQMNSLRAEDTAVYYC
AR<u>DRFRKVHGFDV</u>WGQGTLVTVSS, and a V$_{L-801}$ sequence (SEQ ID NO: 2):
DIQMTQSPSSLSASVGDRVTITC<u>QASQDISNYLN</u>WYQQKPGKAPKLLI
Y<u>DASNLET</u>GVPSRFSGSGSGTDFTFTISSLQPEDIATYYC<u>QQDATFPL</u>
<u>T</u>FGQGTKVEIK, while a second anti-B7-H4 antibody (817) has a V$_{H-817}$ sequence (SEQ ID NO: 3):
EVQLVESGGGLVQPGGSLRLSCAAS<u>GFTFSSY</u>AMHWVRQAPGKGLEWV
SAI<u>SGSGGS</u>TRYADSVKGRFTISRDNSKNTLYLQMNSLRAEDTAVYYC
AR<u>GRWSKWGFDV</u>WGQGTLVTVSS, and a V$_{L-817}$ sequence (SEQ ID NO: 4):
DIQMTQSPSSLSASVGDRVTITC<u>QASQDISNYLN</u>WYQQKPGKAPKLLI
Y<u>DASNLET</u>GVPSRFSGSGSGTDFTFTISSLQPEDIATYYC<u>QQTDNFPY</u>
<u>T</u>FGQGTKVEIK.

In this context, it should be appreciated that while the above V$_H$ and V$_L$ sequences are shown as entire V$_H$ and VL sequences, contemplated V$_H$ and V$_L$ sequences may also be limited to the respective complementarity determining regions (CDRs), which are typically located at about residues 24-34 (L1), 50-56 (L2), and 89-97 (L3) for V$_L$ and at about residues 27-35 (H1), 50-65 (H2), and 95-102 (H3) for V$_H$, and/or those residues from a "hypervariable loop"

(typically located at residues 26-32 (L1), 50-52 (L2), and 91-96 (L3) for $V_L$ and 26-32 (H1), 53-55 (112), and 96-101 (H3) for $V_H$. Viewed from a different perspective, contemplated anti-B7-H4 antibodies may be limited to CDRs and/or hypervariable loop sequences, and as such not necessarily include framework regions (i.e., variable domain residues other than hypervariable loop and CDRs). Furthermore, it should be appreciated that the inventive subject matter is not limited to the exact sequences noted above, but one or more of the sequences may include one or more amino acid changes. Most preferably, the changes will not result in a substantial reduction of specificity and/or affinity. Thus, contemplated sequences will have between 98-99% identity or homology, or between 96-98% identity or homology, or between 92-96% identity or homology, or between 85-92% identity or homology, or between 75-85% identity or homology.

Moreover, it should be noted that contemplated antibodies will expressly include various forms such as monoclonal antibodies, multi-specific antibodies, human antibodies, humanized antibodies, synthetic antibodies, chimeric antibodies, single domain antibodies, single-chain Fvs (scFv), single chain antibodies, disulfide-linked Fvs (sdFv), BiKes, and TriKes as is described in more detail below. Of course, it should also be noted that the term antibody expressly includes all classes of immunoglobulin molecules (e.g., IgG, IgE, IgM, IgD, IgA, and IgY), as well as the corresponding subclasses (e.g., $IgG_1$, $IgG_2$, $IgG_3$, $IgG_4$, $IgA_1$, $IgA_2$).

With respect to contemplated antibody fragments it should be noted that fragments will include one or more portions of an antibody that contains CDRs (typically all CDRs of at least one of $V_H$ and $V_L$), and optionally the framework residues. Thus, antibody fragments will in most cases exhibit an ability to specifically bind to the antigen (here: an epitope of B7-H4). Among other fragments, especially contemplated fragments include Fab', F(ab')$_2$, Fv, scFv, and mutants thereof, naturally occurring variants, as well as fusion proteins with various non-antibody polypeptides (e.g., toxin, antigen recognition site for a different antigen, enzyme, receptor, receptor ligand, etc.). Viewed from a different perspective, contemplated antibody fragments will have an amino acid sequence of at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

In further contemplated aspects, the antibody of fragment thereof may be used for in vitro or in vivo diagnosis and as such be coupled to a detectable label. For example, suitable detectable labels include various enzymes, fluorescent materials, luminescent materials, bioluminescent materials, radioactive materials, positron emitting metals, and nonradioactive paramagnetic metal ions. The detectable label can be coupled or conjugated either directly to the antibody or indirectly, through an intermediate (e.g., chemical or biological linker) using techniques known in the art. Additionally, or alternatively, contemplated antibodies and fragments thereof may also be coupled to a solid support, which is particularly useful for immunoassays or purification of B7-H4 or cells expressing B7-H4. For example, suitable supports include magnetic beads, glass, cellulose, polyacrylamide, nylon, polystyrene, polyvinyl chloride, and polypropylene.

Contemplated antibodies and fragments thereof may also be coupled to or comprise a therapeutic agent to target the agent to a cell expressing B7-H4. For example, especially contemplated therapeutic agents include chemotherapeutic drugs, radionuclide, and immune stimulants (e.g., cytokine, a cytokine analog, a chemokine, or a checkpoint inhibitor). There are numerous manners of preparing antibody-drug conjugates, and all of these are deemed suitable for use herein.

In especially preferred aspects, contemplated antibodies or fragments thereof may also be prepared as chimeric proteins in which at least one portion of the antibody is continuous with a second polypeptide (optionally via a preferably flexible linker). For example, suitable chimeric proteins may be configured as chimeric antigen receptors that may have an intracellular signaling portion, a transmembrane portion, and an extracellular recognition domain. In such case, it is generally contemplated that the recognition domain includes an antibody fragment (e.g., scFv or single domain) and/or that the intracellular signaling domain comprises an activating/ITAM motif Among other options, such chimeric antigen receptors are preferably expressed in cytotoxic immune competent cells, and especially in NK cells and/or T cells.

On the other hand, and especially where the anti-B7-H4 antibody or fragment thereof is used to additionally mediate cell or receptor/ligand contact, contemplated chimeric proteins may be constructed as a bispecific fusion protein, as a bispecific killer cell engager (BiKE), or as a trispecific killer cell engager (TriKe). For example, a bispecific fusion protein may comprise the anti-B7-H4 antibody or portion thereof and a second affinity ligand that selectively binds to a desired target. Such target may be a soluble protein or a cell-bound protein, and especially contemplated targets include PD-L1. On the other hand, contemplated chimeric molecules may be constructed as bispecific polypeptides (e.g., first scFv coupled via linker to second scFv) in which one portion comprises the anti-B7-H4 antibody or portion thereof and in which the other portion has a binder to a marker specific for an immune competent cell (e.g., anti-CD3).

In further contemplated aspects, the anti-B7-H4 antibody or portion thereof may also be coupled to an IgG-Fc/IL15Ra/IL15 hybrid (e.g., ALT803). For example, the anti-B7-H4 antibody fragment could be a scFv portion that is coupled to one or both arms of the hybrid to so form a TxM (see TxM technology at URL:Altorbioscience.com). Or the anti-B7-H4 antibody fragment could be a scFv portion that is coupled to one arm of the hybrid, while the other arm of the hybrid could be a scFv portion that binds PD-L1 (or other immune related ligand).

As should be appreciated, nucleic acids encoding contemplated anti-B7-H4 antibodies are also expressly considered herein, and the skilled artisan will be readily able to prepare such nucleic acids (e.g., DNA, RNA) and recombinant entities comprising such nucleic acids. Among other options, suitable recombinant entities include yeast, bacterial, and viral expression vectors, linear DNA for genome editing or other integration, etc.

As will be readily appreciated, use of anti-B7H4 antibodies, fragments thereof, or chimeric proteins containing anti-B7H4 antibodies or fragments thereof is particularly advantageous where immune suppression mediated by B7H4 is to be reduced or inhibited. For example, it is known that various immune competent cells (especially antigen presenting cells) that express B7H4 on their surface reduce T cell stimulation (e.g., T cell proliferation, cytokine secretion) as well as lead to increased Treg cells. Consequently, antibodies or portions thereof can be especially useful in the reversal or reduction of immune suppression via B7H4 signaling. Moreover, as at least some cancer cell also express and display B7H4, and so offer a further therapeutic target (e.g., via targeting with a chimeric molecule that has a B7H4 binding portion and an immune stimulatory portion (e.g., ALT-803)).

Inflammatory cytokines and other cytokines and/or factors within the tumor microenvironment (e.g., IL-2, IL-6, IL-10, IFN-α, IFN-γ, TNF-α, and hypoxia) have been shown to induce B7-H4 expression on both tumor cells and monocytes/macrophages. Additionally, activated T cells have been shown to express the B7-H4R via specific binding of B7-H4 Ig, which also modulates T cells function via decreasing inflammatory T-cell responses while increasing Treg function. In the case of tumor and tumor-associated macrophage expressed B7– H4, the interaction of the B7-H4R-expressing T cells with B7-H4-expressing tumor cells or tumor-associated macrophages would decrease the inflammatory and proliferative response by the T cells, while increasing the number and function of the Treg cells. Therefore, it should be appreciated that blocking of B7H4 signaling will maintain an inflammatory T-cell response within the tumor microenvironment. Still further, soluble B7H4 may be reduced or eliminated using contemplated antibodies or constructs presented herein.

Moreover, the inventors have also discovered that the glycosylation status of B7H4 is associated with biological activity of B7H4, and that the IgV and IgC domains have distinct (but also cooperative) functions as is provided in more detail below. Notably, the inventors discovered that glycosylation of B7H4 directly affects function of B7H4. For example, the deglycosylated form of B7H4 completely abolished effects of B7H4 on T cell proliferation. To further investigate the specific role of N-glycosylation, the inventors also prepared various mutant forms of the extracellular domain of B7H4. More specifically, the asparagine residues located in the IgC domain (N160, N190, N196, N205, N216 and N220) were mutated out for glycine in various permutations, and their functionality was evaluated as is also described in more detail below. Notably, N-glycosylation had no substantial effect on binding to T cells. Even more intriguing, most deglycosylated forms of B7H4 suppressed T cell proliferation, an effect that was abrogated when the entire IgC domain was deglycosylated.

Consequently, it should be appreciated that various compositions with mutant forms of B7H4 (extracellular or entire molecule) could be used as a therapeutic modality to reduce or otherwise influence inhibition of T cell proliferation normally observed with B7H4. In an effort to further delineate functions between the IgC and IgV domains, the inventors also tested individual binding capability of the IgC and IgV domains to T cells. Notably, both IgV and IgC domains were retained independently and non-competitively, suggesting the existence of two different receptors or binding sites for B7H4 on the surface of activated T cells.

In yet further aspects of the inventive subject matter, the inventors tested which domain would be responsible for suppression of T cell proliferation and control of the pro-inflammatory cytokines production. Interestingly, the IgV domain was a considerably better suppressor of $CD4^+$ T cell proliferation than B7H4, the IgC domain or both domains together. At the same time, IgC was more potent than IgV in suppressing $CD8^+$ cells, once more pointing to distinct actions of these domains with respect to $CD4^+$ and $CD8^+$T cells. Additionally, IgC showed a more pronounced biological effect on formation of Tregs from T cells as compared to IgV.

In view of these findings and as also further contemplated below, the inventors also contemplate use of various recombinant B7H4 molecules and pharmaceutical compositions comprising same. Most typically, such recombinant proteins may be soluble forms of B7H4, including a recombinant soluble extracellular domain, or a soluble single domain (e.g., IgC or IgV only), which may have one or more mutations (e.g., N→G) to eliminate N-glycosylation of the mutant protein. Most typically such B7H4 protein will be based on a human sequence of B7H4 and all of its isoforms and consensus forms, which can be found at Uniprot at the accession number Q7Z7D3.

For example, recombinant B7H4 may be expressed in an antigen presenting cell together with one or more antigens for which tolerance is desired. Co-expression and co-presentation of the antigen and the recombinant B7H4 is thought to induce immune suppressive conditions to reduce, for example, allograft rejection or autoimmune conditions. On the other hand, deglycosylated forms of the extracellular domain(s) of B7H4 can be produced and administered to bind to the receptors on T cells and so competitively reduce binding of B7H4 from an APC, which is thought to reduce immune suppression against an antigen presented by the APC.

Therefore, co-expression of underglycosylated or deglycosylated forms of B7H4 with an antigen (e.g., tumor antigen) is believed to increase an immune response against the antigen due to lack of immune suppression.

Experiments

Figure 1:
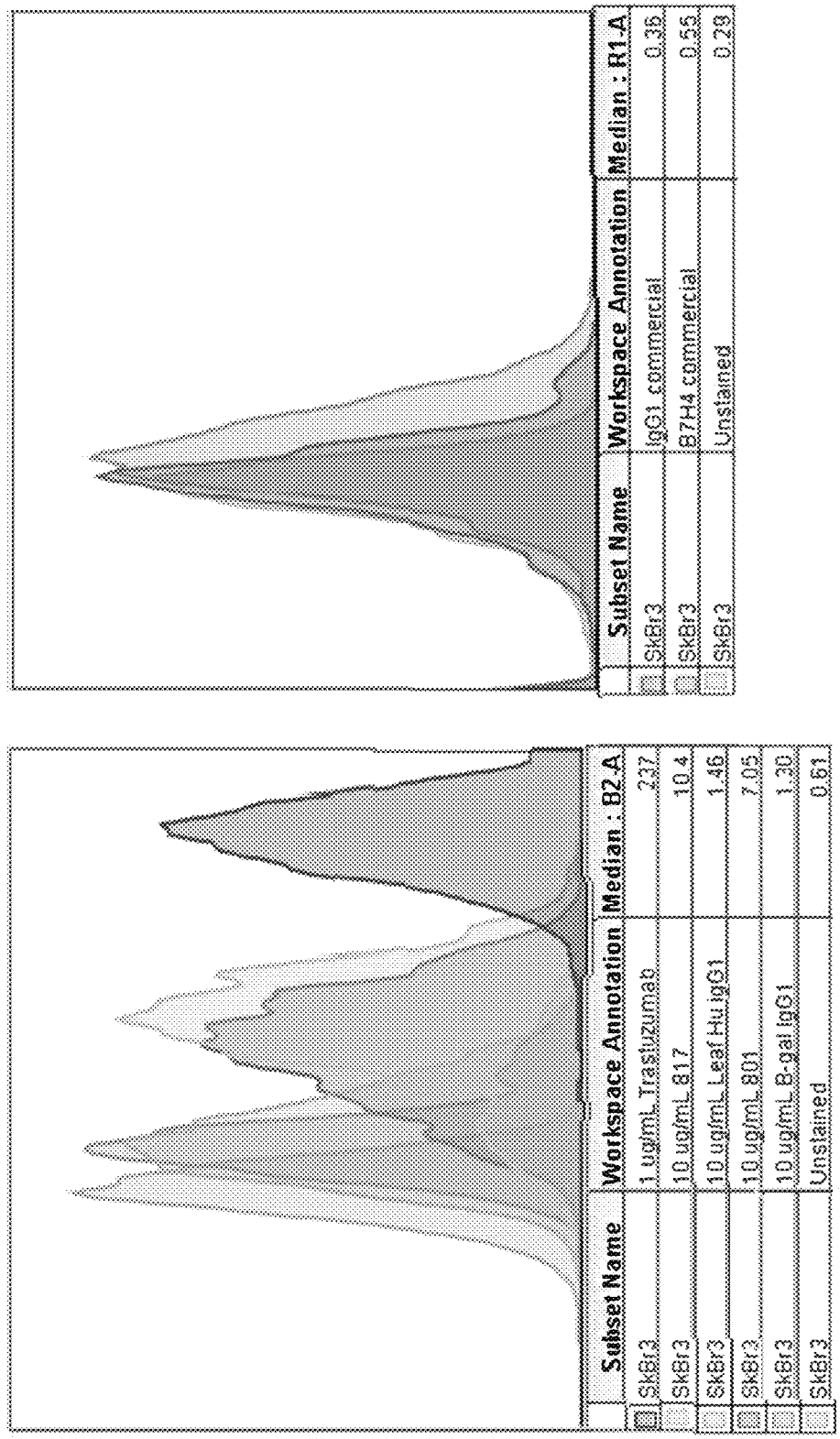
FIG. 1 is a graph depicting exemplary relative staining intensities for the anti B7-H4 antibodies according to the inventive subject matter, along with positive and negative controls.

Anti-B7H4 Antibodies:

To isolate antibodies against B7H4, the inventors used B7H4 protein in RNA display selection of binders following protocols well established in the art (see e.g., ACS Comb Sci. 2013 Feb 11; 15(2): 77-81.). Best binders were then evaluated for binding strength and kinetics as is described below. FIG. 1 exemplarily illustrates binding of two exemplary anti-B7-H4 antibodies (801 and 817) to B7-H4 expressed on the human breast cancer cell line SkBr3. As can be seen from the left panel of FIG. 1, the positive control binding of trastuzumab to Her2 on the SkBr3 was strongly detected at a concentration of 1 ug/ml, and 801 and 817 provided strong binding signals at 10 ug/ml. The unstained negative control was below and near negative controls using B-gal and Leaf IgG1. As can also be seen from the right panel of FIG. 1, commercial anti-B7-H4 antibodies did not produce a strong signal versus control as compared to the anti-B7-H4 antibodies presented herein.

Figure 2A:
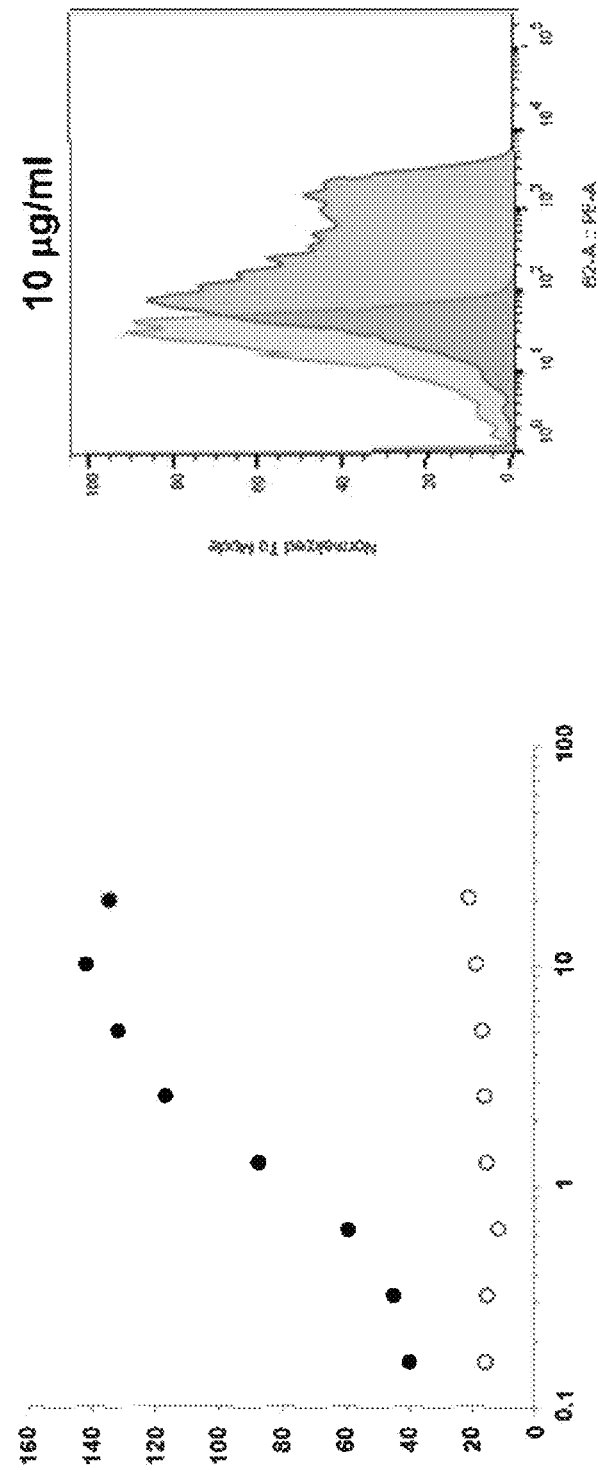
FIG. 2A is a graph depicting EC50 data for one exemplary anti B7-H4 antibody to a cell transfected with B7-H4.
Figure 2B:
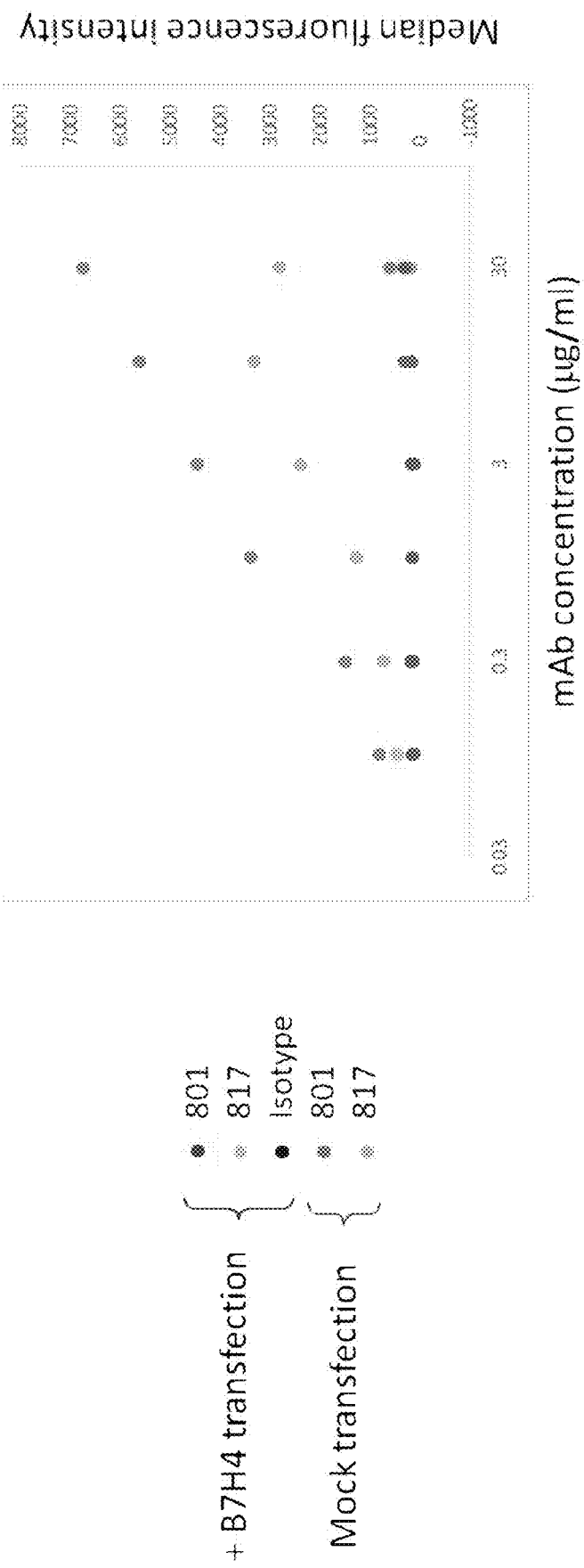
FIG. 2B is a graph depicting comparative binding of 801 and 807.
Figure 2C:
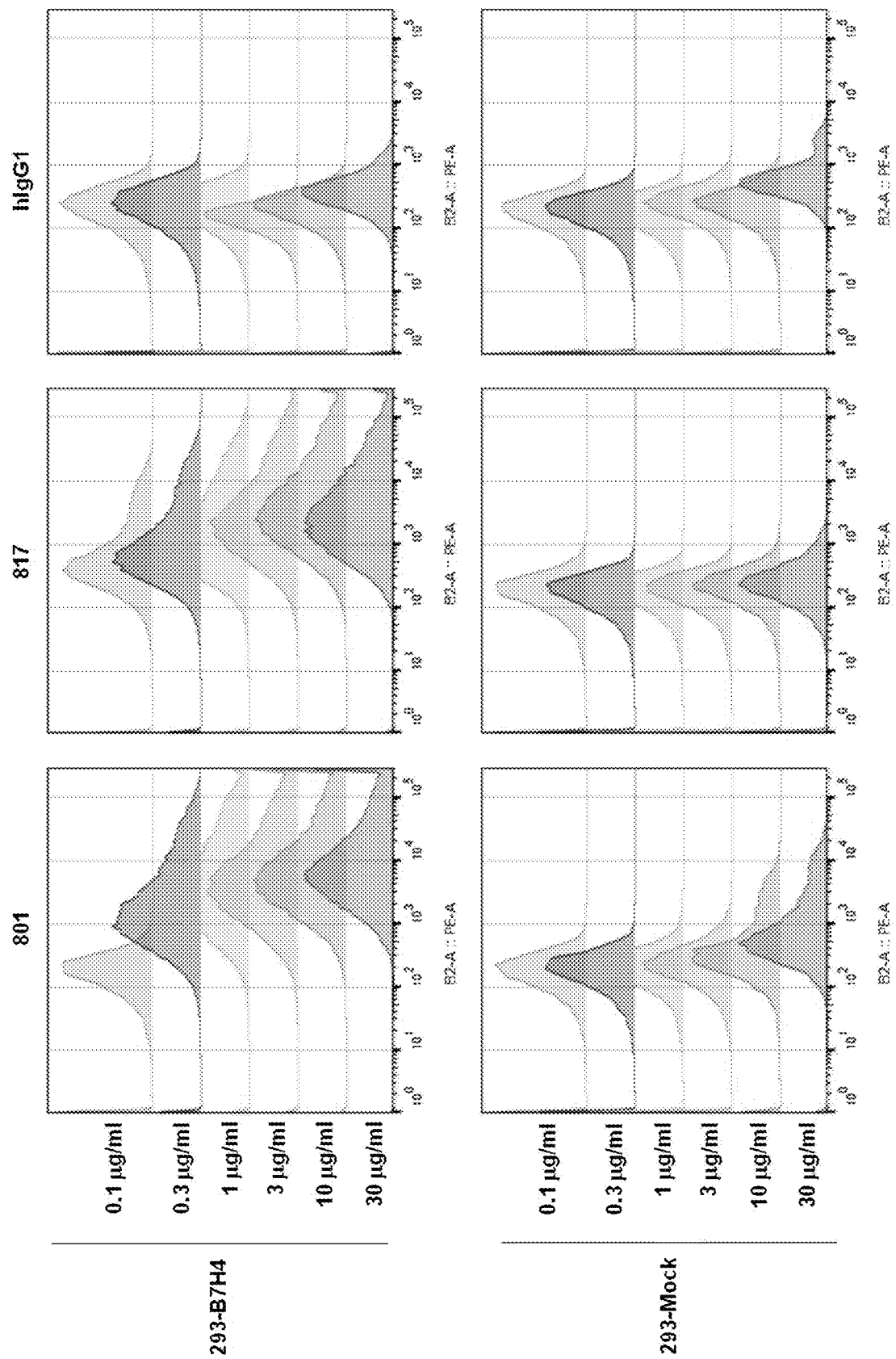
FIG. 2C depicts raw data for FIG. 2B.
Figure 3:
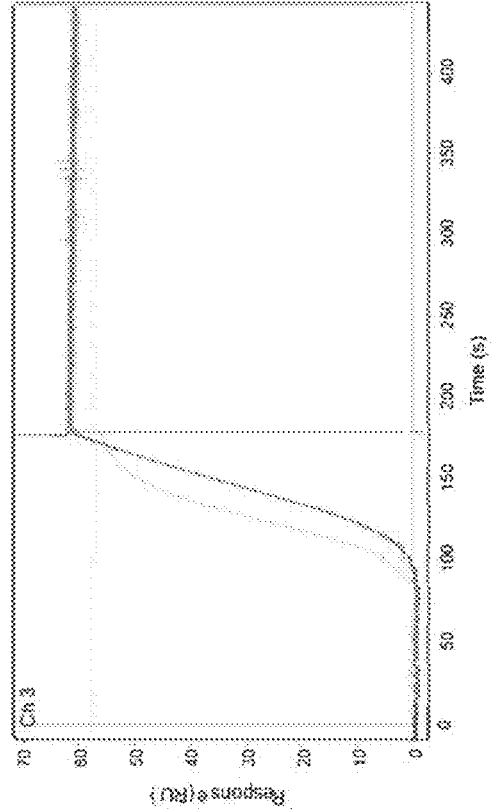
FIG. 3 is a graph depicting exemplary data of one SPR experiment using anti B7-H4 antibodies according to the inventive subject matter.
Figure 3:
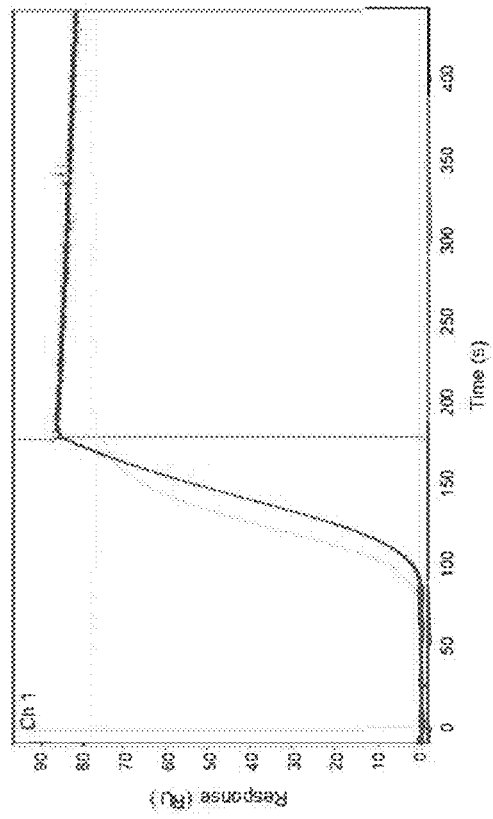
Figure 4:
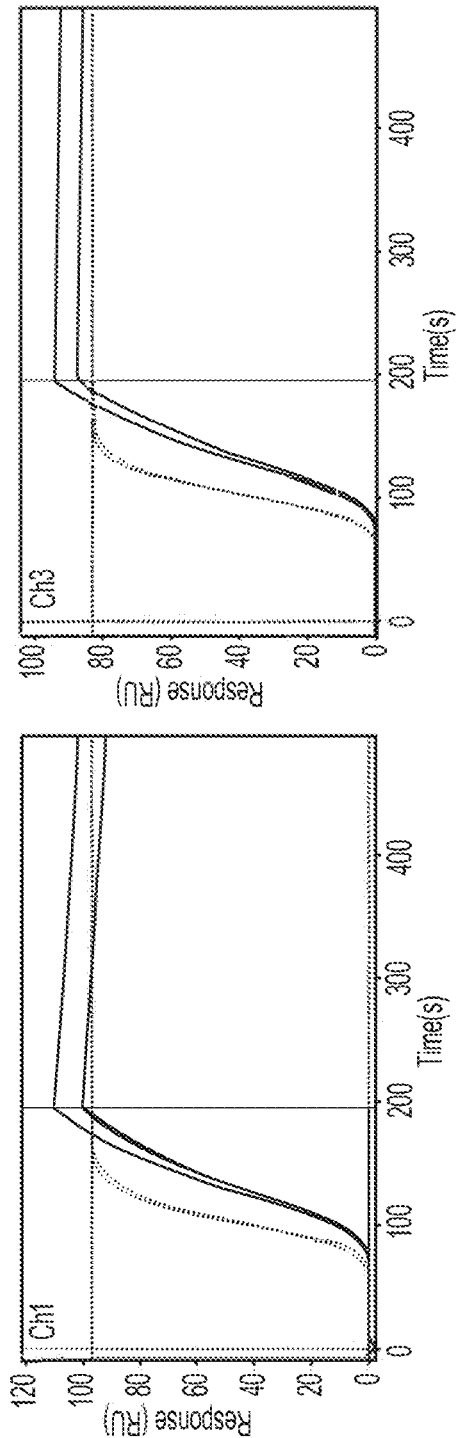
FIG. 4 is a graph depicting exemplary data of another SPR experiment using anti B7-H4 antibodies according to the inventive subject matter.
Figure 5:
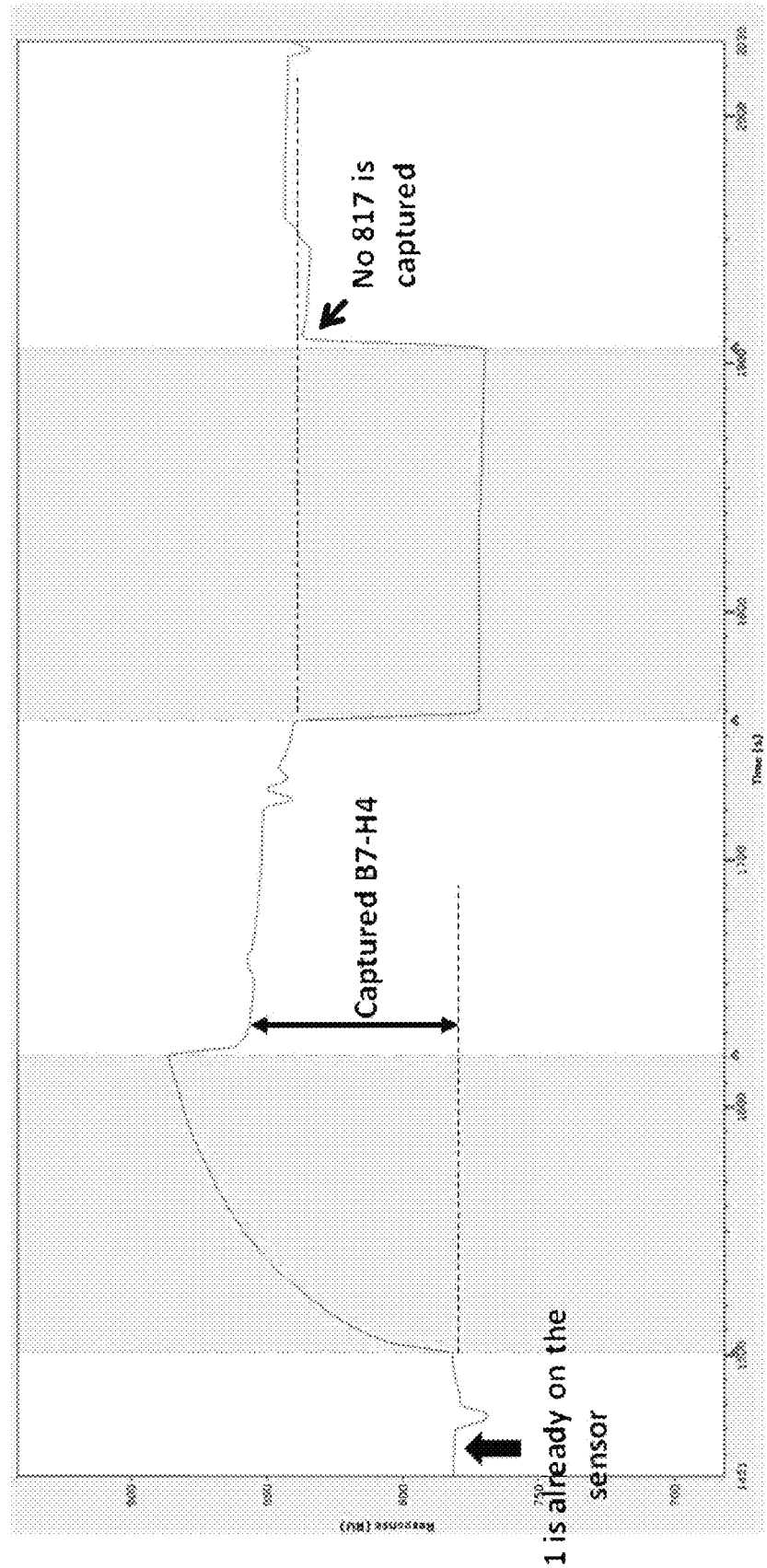
FIG. 5 is a graph depicting exemplary data of a further SPR experiment illustrating common epitope binding for the anti B7-H4 antibodies according to the inventive subject matter.

To ascertain binding specificity of exemplary anti-B7-H4 antibodies presented herein, the inventors transfected 293T cells with a recombinant expression plasmid that encoded B7-H4 clone 801. As is readily evident from FIG. 2A, the anti-B7-H4 antibody 801 strongly bound to the expressed B7-H4. FIG. 2B depicts the same experimental setup comparing binding of 801 and 817, while FIG. 2C shows the raw data for FIG. 2B. Binding kinetic parameters were then established for both 801 and 817 anti-B7-H4 antibodies as is further exemplarily shown in FIGS. 3 and 4 using surface plasmon resonance. As is evident from these data, both antibodies bound at a KD with below sub-nanomolar affinity. Finally, the inventors used surface plasmon resonance to determine if the two antibodies would bind the same epitope. The results of FIG. 5 strongly suggests that the bind is overlapping or at the same epitope of B7-H4. Here, the B7H4-801 antibody was on the sensor and exposed to soluble B7H4. As can be seen, complex formation was rapid and specific to B7H4. After washout, B7H4-801 antibody was added to the chip. However, no additional binding was observed, indicating that the binding sites for the B7H4-801 antibody and the B7H4-817 at least partially overlap.

B7H4 Glycosylation and Domain Activity:

Deglycosylated/hypo-glycosylated form of B7-H4 as competitive antagonist: The inventors further investigated the role of B7-H4's Ig-like domains as well as the N-linked glycosylation in their co-inhibitory function using domain-specific deletions and site-directed mutagenesis. More particularly, the inventors generated a set of mouse B7-H4 protein mutants, engineered either to contain only one of its two domains, or carrying one or more point mutation(s) of potential glycosylation sites. The inventors then evaluated the ability of these mutant proteins to bind to T cells in culture and the impact of the mutant proteins on the T cell proliferation and cytokine production.

Most notably, the inventors found that: 1) B7-H4 has seven N-glycosylation sites; 2) B7-H4 glycosylation is crucial for membrane trafficking, folding, and/or functionality; and 3) both individual domains of B7-H4 bind independently to pre-activated T cells triggering distinct processes in different subsets of T cells. As can be seen below, the IgV domain was more efficient in suppressing proliferation of conventional T cells, while the IgC domain predominantly inhibited cytokine production. In addition, the IgC domain increased the frequency, proliferation, and de-novo induction of functional Tregs. Moreover, unlike the full-length B7-H4, mixtures of both domains delivered synergistic effect on Treg induction but the functionality of these Tregs, measured by the suppression of T effector cells, is equivalent to the activity of IgC only. Finally, the inventors found that these effects are also true for human T cells, but with the twist that the IgC seems to be more robust inhibitor of human T cell proliferation than IgV.

Figure 6:
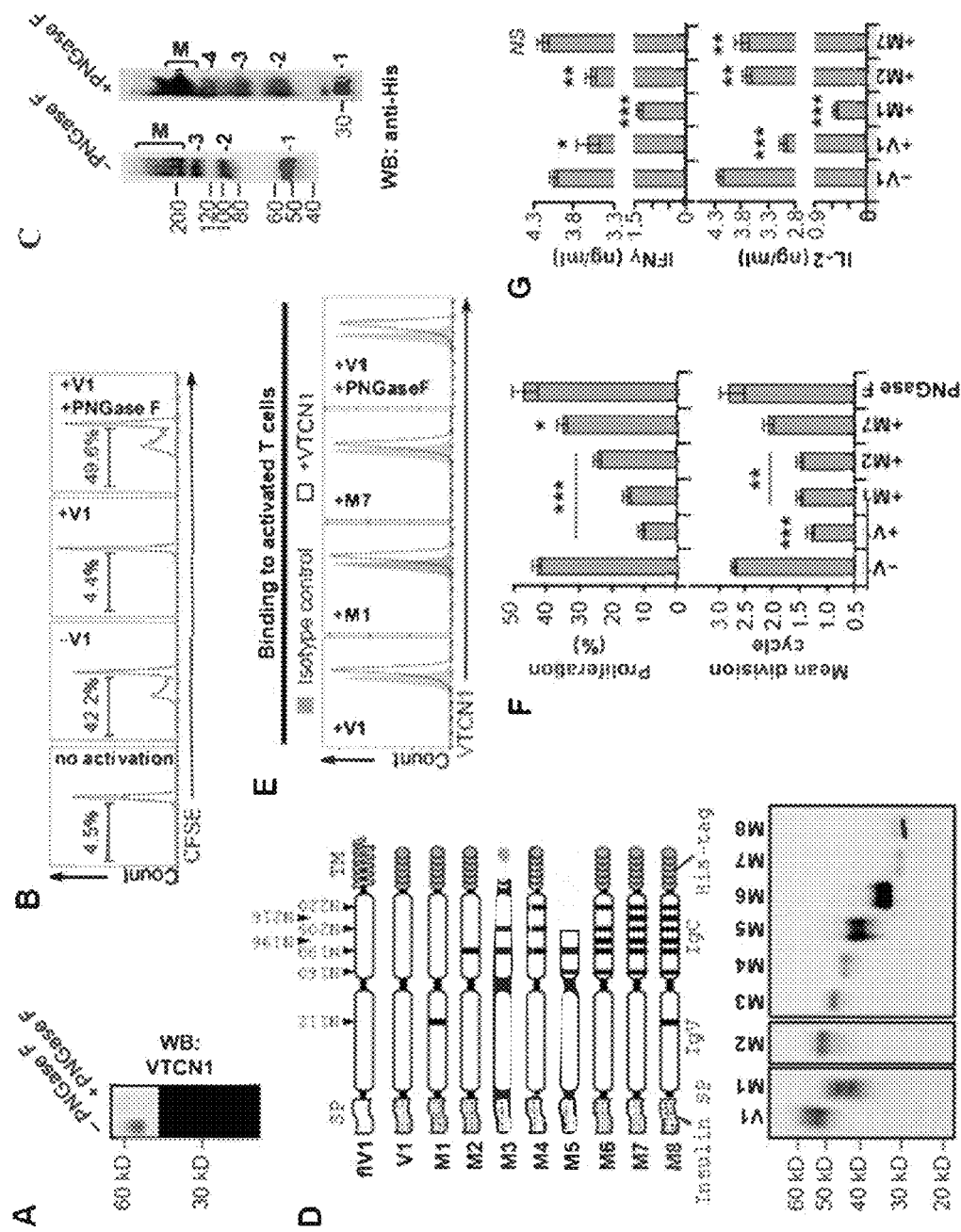
FIG. 6 Panel A is a western blot of recombinant B7-H4 (10 ng/lane) after treatment with buffer or PNGase F (5 U/g protein). Western blot of recombinant B7-H4 (10 ng/lane) after treatment with buffer or PNGase F (5 U/g protein); Panel B shows a proliferation assay of CD3+T cells by wild-type or deglycosylated B7-H4. CFSE labeled CD3+T cells isolated from spleens of 9 NOD mice were treated with buffer, 10 pg/ml of B7-H4 (V1) or PNGase F-treated V1 and then activated with CD3 and CD28 antibodies for 5 days. Proliferation was assessed by CFSE dilution and indicated as proliferating percentages of total live T cells; Panel C is a western blot analysis of B7-H4 dimerization. Western blots analysis of B7-H4 dimerization. Recombinant B7-H4 and deglycosylated B7-H4 were incubated for 30 min at 4° C. in the presence of $BS^3$ cross-linker and then analyzed by SDS-PAGE for oligomerization; Panel D shows a schematic diagram of B7-H4 mutants and a western blot of expression of those mutants in HEK cells. Upper panel—schematic representation of B7-H4 N-glycosylation mutants generated by Asn (N) to Gly (G) switch in either single or multiple predicted sites. Each arrowhead indicates position of a mutation site. Lower panel—western blot of conditioned media (V1 and M1-M7) from HEK cells stably expressing the indicated mutant 6×His-tagged construct. M8 was detected in cell lysate from HEK-transfected cells; Panel E is a FACS analysis of B7-H4 binding to T cells. Pre-activated CD3+T cells were incubated with V1 (10 pg/ml) or indicated glycosylation mutant and then cells were stained with anti-His$^6$ and analyzed by FACS. Black line—anti-His; Gray shade—isotype control; Panel F shows quantification of the percentages of proliferating T cells activated in the presence of indicated recombinant protein.

B7-H4 is heavily glycosylated protein with an apparent molecular weight of 55 kDa, almost twice as the predicted from the primary sequence per se. Treatment of endogenously overexpressing B7-H4 cancer cell lines with PNGase F reduced the size of the protein to the expected 28 kDa indicating that B7-H4 is N-glycosylated. To validate these results in vitro, the inventors cloned the extracellular portion of B7-H4 in frame with a C-terminal 6×His-tag and insulin signal peptide (V1) and purified the recombinant protein from conditioned medium of stably transfected HEK cells. As shown in FIG. 6, treatment of V1 with PNGase F clearly showed a shift of the protein's molecular weight to its predicted size. To test the role of N-glycosylation on B7-H4's T cell suppression function, CFSE-labeled murine Pan T cells were activated with anti-CD3 and anti-CD28 in the presence of either glycosylated or PNGase F-deglycosylated V1 (10 µg/ml), and then their proliferation was analyzed by FACS (shown in FIG. 6). The results showed that unlike glycosylated V1, which reduced significantly T cell proliferation, deglycosylation completely abolished V1 functionality. Since N-glycosylation have been reported to alter oligomerization of cell surface molecules thus affecting their biological activities, the inventors also investigated dimerization status of purified V1 using bis(sulfosuccinimidyl)suberate ($BS^3$) cross linker to stabilize protein dimers/multimers. The inventors found that V1 could indeed dimerize, however pharmologically deglycosylated V1 was also able to oligomerize to a similar degree (shown in FIG. 6).

The results using PNGase F treatment suggested that N-glycosylation takes part in modulating B7-H4 biological activity, but did not reveal the number of glycosylation sites and the role of each glycosylated Asn residue for the function of B7-H4. To answer these questions, first the inventors analyzed the amino acid sequence for potential glycosylation sites using the Eukaryotic Linear Motif (URL: elm.eu.org/). The database predicted six highly probable N-glycosylation Asn residues, all located in the IgC-like domain (N160, N190, N196, N205, N216 and N220), and one poorly scoring with the structural filter Asn in the IgV like domain (N112). Next, the inventors generated V1 DNA constructs carrying point mutations at a single (M1 and M2) or multiple (M3 to M8) potential glycosylation sites changing those residues from Asn to Gly. FIG. 6 (top panel) shows a schematic of the full length B7-H4 (flV1) in comparison to the generated recombinant, soluble proteins. Constructs carrying single point mutations in every predicted glycosylation site were also made but only M1 (the potential glycosylation site in IgV) and M2 (N190G, one of the six predicted glycosylation sites in IgC) are shown since all other single mutants had very similar properties (data not shown). These constructs were expressed in HEK cells and the molecular weight of the recombinant proteins released in conditioned media was analyzed by western blot. The results revealed that all seven potential glycosylation sites of B7-H4 are utilized and when all of them are destroyed, the molecular weight of the resultant protein (M8) is identical to the PNGase F-treated V1.

Figure 12:
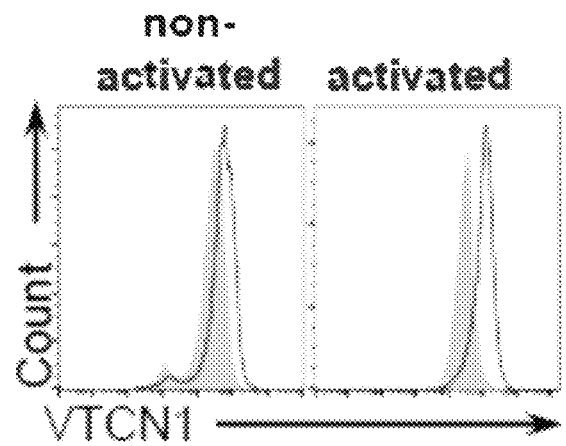
FIG. 12 shows FACS analysis of non-activated and pre-activated NOD T cells. Isolated Pan T cells were incubated with V1 and the protein retained on the cell surface was revealed with anti-6×His-FITC.

Next, the inventors isolated these V1 mutated proteins from conditioned media by Ni-NTA affinity purification to examine their functionality. Previous reports showed that upon activation, T cells upregulate their putative B7-H4 receptor(s). The inventors observed similar results in a binding assay where V1 was incubated with pre-activated or non-activated T cells and then its retention was assessed by FACS (see FIG. 12). Next, the inventors used this binding assay to test every N/G mutant (see FIG. 6). The M8 mutant was not included in this experiment because this protein was not secreted; hence, as a control for completely deglycosylated B7-H4 the inventors used PNGase F-treated V1. Interestingly, M1 (deglycosylated IgV-like domain), M7 (deglycosylated IgC-like domain) and PNGase F-treated V1 had a similar degree of retention by T cells as V1, showing that the glycosylation status of B7-H4 has no effect on T cell binding.

The inventors then determined the effect of B7-H4 deglycosylation on T cell proliferation (see FIG. 6). Deglycosylation in a single site, either in the IgV or IgC domain (represented by M1 and M2), suppressed T cell proliferation very similarly to V1 (FIG. 6). However, deglycosylation of the entire IgC domain (M7) reduced significantly the ability of B7-H4 to control T cell proliferation. Interestingly, M1 inhibited secretion of the pro-inflammatory cytokines IFNγ and IL-2 more than V1; therefore, the control of T cell proliferation is not reliant only on the cytokines' secretion. At the same time, treatment with M7 did not affect secretion of IFNγ and just slightly alleviated IL-2 (see FIG. 6G, depicting ELISA analysis of secreted IFNγand IL-2 in conditioned media from activated T cells treated with the indicated B7-H4 mutants) showing that the most probably the overall glycosylation of IgC domain is crucial for the control of T cell activation by B7-H4.

Figure 7:
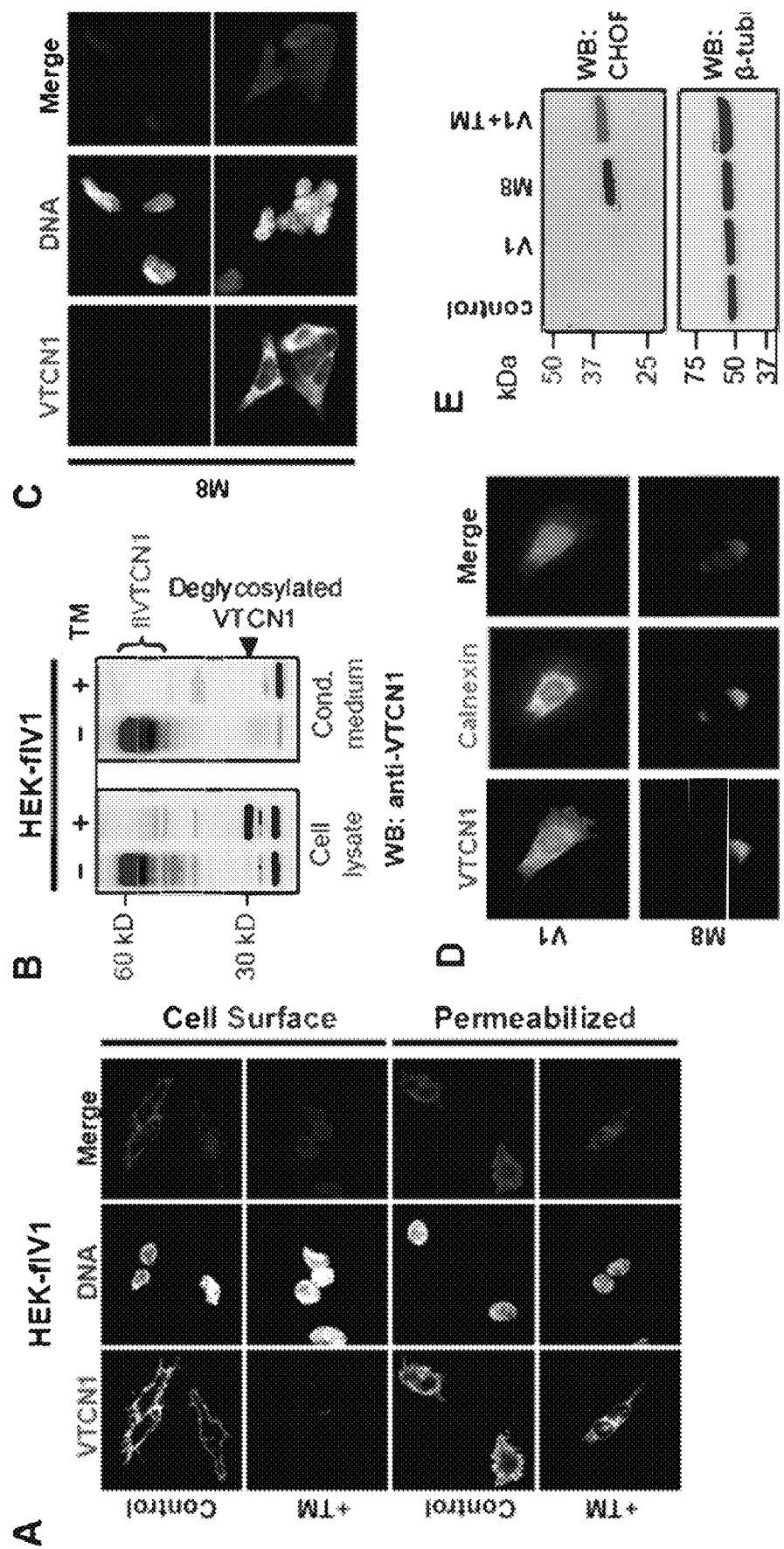
FIG. 7 shows various immunofluorescence or western blot analysis evidencing that B7-H4 glycosylation is crucial for protein's trafficking and folding. (A) Upper panel —Immunofluorescence of full length B7-H4 in transfected cells (HEK-flV1) after treatment with buffer (Control) or 5 μg/ml tunicamycin (TM). Cells were fixed with and then stained after treatment with (permeabilized) or without (cell surface) 0.1% Triton X-100. Lower panel —Immunofluorescence of cell surface's B7-H4 in peritoneal macrophages isolated from DBA mice after treatment with buffer or TM. (B) Western blots of cell lysates (right lanes) and conditioned medium (left lanes) from B7-H4-transfected HEK cells after treatment with or without tunicamycin. (C) Cell surface and intracellular immunostaining of deglycosylated B7-H4 construct (M8) in transiently transfected HEK cells. (D) HEK cells transfected with V1 or M8 were stained for B7-H4 and calnexin (ER marker). (E) Western blot analysis for the ER stress marker, CHOP, in HEK cells transfected with either a V1 or M8 construct. V1+TM–V1–transfected cells treated with tunicamycin. Beta-tubulin was used as a loading control.
Figure 13:
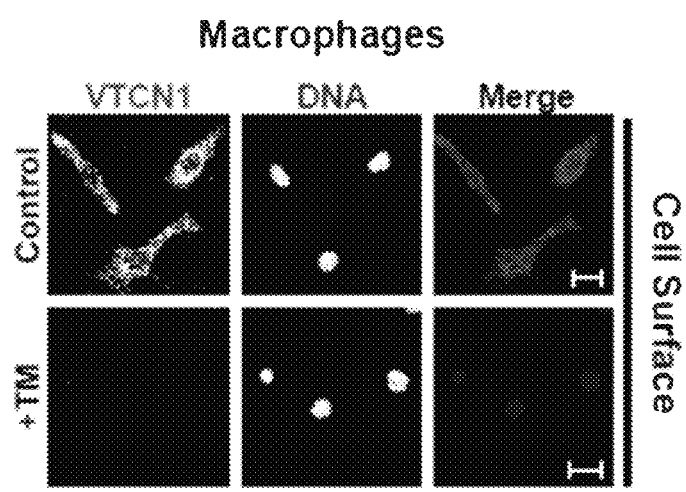
FIG. 13 shows immunofluorescence of peritoneal NOD macrophages that were treated ON with buffer (control) or tunicamycin(TM) and then stained for B7-H4.

After generation of B7-H4 mutants, the inventors found that the non-glycosylated mutant (M8) is not secreted and a stable cell line expressing this protein could not be produced. The inventors contemplated that such instability is due to folding and/or trafficking defects, which are rooted from the deglycosylation of B7-H4. To address this possibility, the inventors treated HEK cells stably expressing fiV1 with tunicamycin (TM) and then examined its presence on the cell surface (as shown in FIG. 7). TM treatment resulted in complete loss of cell surface's B7-H4. Analysis of endogenous B7-H4 expressed by peritoneal NOD macrophages provided similar results, showing that this is neither a cell type specific event, nor a result from B7-H4 overexpression (as shown in FIG. 13). Moreover, immunoblot analysis of cell lysates and conditioned media confirmed that TM treatment leads to a complete deglycosylation and halted secretion of B7-H4 (FIG. 7).

In agreement with these results, transient transfections with M8 showed that this mutant remains exclusively inside of the cells and dominantly resides in the endoplasmic reticulum (ER) as evident by the co-localization staining with the ER marker calnexin (as shown in FIG. 7). The inventors found that M8 leads to ER stress, indicated by the enhanced expression of CHOP protein in cell lysates from M8− but not in B7-H4-transfected cells (as shown in FIG. 7), showing that B7-H4 glycosylation, as a whole, is critical for its folding and secretion.

Thus, N-linked glycosylation is one of the significant features of B7-H4 molecule, and particularly asparagine residues that are glycosylated in B7-H4: N112, N160, N190, N196, N205, N216 and N220. Interestingly, the inventors observed that the mutation in N112 (N112G) leads to more significant drop in molecular weight of B7-H4 (FIG. 6) than any other single mutation site, which might be due to a significantly different glycan's profile at this position. Moreover, the half-life of Ni 12G mutant was considerably extended in comparison to B7-H4 (see FIG. 15) showing that this site is important for B7-H4 stability. The glycosylation on N112 did not appear to have significant effects on B7-H4 T cell suppression functions even though the extended lifespan of N112G might be the reason for the drop in pro-inflammatory cytokine secretion (FIG. 6). The fact that IgC domain had a similar to N112G effects (lower inhibition towards T cell proliferation in comparison to B7-H4 but stronger effect on cytokine secretion)(FIGS. 6, and 8) points that the glycosylation at IgV might be crucial factor that controls the activity of IgC domain. At the same time, the individual glycosylation sites at IgC domains seemed irrelevant for the function of B7-H4 but removal of multiple glycosylation sites reduced the activity of B7-H4 (FIG. 6), suggesting that the glycosylation as a whole, at least in the IgC domain, but not at a specific site is essential for its biological activity.

Further, such experimental results strongly suggest that N-glycosylation is crucial for trafficking and membrane location of some proteins. In agreement with this, complete loss of glycosylation of B7-H4 ablated the cell surface expression and secretion. This was most probably due to improper folding, a conclusion supported by the exclusive co-localization of deglycosylated B7-H4 with the ER chaperone protein calnexin. Calnexin interacts strongly to proteins with a significant loss of glycan chains, an important step in the unfolded protein response (UPR). Prolonged accumulation of unfolded B7-H4 proteins leads to higher cell death, probably a result of irreversible ER stress and up-regulation of pro-apoptotic proteins such as CHOP. Taken together the results showed that the N-linked glycosylation mediates B7-H4 cell surface localization.

Thus, in yet another aspect of the inventive subject matter, the inventors contemplate a pharmaceutical composition that includes an extracellular portion of a hypo-glycosylated mutant form of B7-H4 that can act as a competitive antagonist of endogenous B7-H4. Use of such mutant protein will advantageously bind to the T cells without triggering secretion of suppressive cytokines and/or Treg development. As used herein, the hypo-glycosylated mutant form of B7− H4 refers to any modified B7-H4 protein or portions thereof that has less N-glycosylation residues (e.g., via enzymatic removal) or has at least one or more modified N-glycosylation residues such that the number of N-glycosylation in such molecule is reduced as compared to wild-type B7-H4. Thus, the hypo-glycosylated mutant form of B7-H4 has at least one, preferably at least three, more preferably at least five N-glycosylation residues among N112, N160, N190, N196, N205, N216 and N220 modified to a non-glycosylation amino acid (e.g., glycine, etc.). In some embodiments, the modified N-glycosylation residues may include one N-glycosylation residues in the IgV domain (N112). In other embodiments, it is also contemplated that all modified N-glycosylation residues are placed in the IgC domain (selected from N160, N190, N196, N205, N216 and N220).

Any suitable length of extracellular portion of a hypoglycosylated mutant form of B7-H4 that can sufficiently bind to a T cell receptor to so competitively inhibit wild type, endogenous B7-H4 are contemplated. Preferably, the extracellular portion of a hypo-glycosylated mutant form of B7-H4 includes at least 60%, at least 70%, at least 80%, at least 90% of the entire extracellular domain (including IgV, IgC, signaling sequence and/or stalk domain that are placed to N-terminus of transmembrane domain).

In some embodiments, the extracellular portion of a hypo-glycosylated mutant form of B7-H4 can be coupled with a pharmaceutically acceptable carrier. One exemplary carrier includes nanoparticles to which the recombinant proteins can be directly or indirectly linked.

The nanoparticles can be a bead or a protein molecule that can be conjugated (or linked) with the recombinant peptide. For example, suitable nanoparticles may include protein A, protein G, protein Z, albumin, and refolded albumin. Especially, where the carrier protein is albumin, the hydrophobic recombinant peptide may fit in one of Sudlowsite I and II of the albumin or any other hydrophobic area of the albumin. In other embodiments where the recombinant peptide is not hydrophobic enough, it is contemplated that the recombinant peptide can be coupled with an hydrophobic short anchor peptide (in a length of at least 10 amino acids, 15 amino acids, 20 amino acids, 30 amino acids, etc.) such that the recombinant peptide can be placed at the Sudlow's site I and II of the albumin via the hydrophobic short anchor peptide.

In still further embodiments, the extracellular portion of a hypo-glycosylated mutant form of B7-H4 can be coupled with an IL-15 superagonist (e.g., ALT-803 or TxM, etc.). For example, where the extracellular portion of a hypo-glycosylated mutant form of B7-H4 is coupled to a TxM (i.e., ALT-803 plus an affinity portion such as a scFv), the inventors contemplate that the extracellular portion of a hypo-glycosylated mutant form of B7-H4 is coupled to at least one of the cytokine (IL-15) or the cytokine binding domain (IL-15R). In such example, it is further preferred that at least one of the cytokine (IL-15) or the cytokine binding domain (IL-15R) is coupled to a binding motif to a tumor-associated antigen, preferably a patient-specific and/or tumor-specific neoepitope. As used herein, the tumor-associated antigen refers any antigen that can be presented on the surface of the tumor cells, which includes an inflammation-associated peptide antigen, a tumor associated peptide antigen, a tumor specific peptide antigen, and a cancer neoepitope. Alternatively or additionally, it is also contemplated that the at least one of the cytokine (IL-15) or the cytokine binding domain (IL-15R) is coupled to a dendritic cell targeting moiety, for example, a binding molecule to a mannose receptor (e.g., CD206), which is a hallmark molecule for immature dendritic cells. While any suitable binding molecules that can specifically recognize at least a portion of the mannose receptor (preferably human mannose receptor) are contemplated, a preferred binding molecule includes a mannose-derived polysaccharide (e.g., mannose-dextran, mannan, lipoarabinomannan, etc.), fucose-derived/containing polysaccharide, or N-acetylglucosamnine-derived/containing polysaccharide, or any other mannose receptor interacting molecules (e.g., agalactosyl IgG, etc.), which may facilitate uptake of the recombinant protein into the dendritic cell upon binding to the mannose receptor.

Optionally, the extracellular portion of a hypo-glycosylated mutant form of B7-H4 can be coupled to the TxM via a linker or a spacer. The linker can be a non-cleavable linker that is typically between 3-30 amino acids, preferably between 5-20 amino acids, more preferably between 5-15 amino acids. Preferably, such linker is glycine-rich sequences (e.g., gly-gly-ser-gly-gly, etc.) to provide structural flexibility between the cytokine binding domain (or cytokine) with the extracellular portion of a hypo-glycosylated mutant form of B7-H4. Alternatively, the linker can be a linker that can be preferably cleaved in the tumor microenvironment. While any suitable linkers that can be preferentially cleaved in the tumor microenvironment and/or upon activation of immune system are contemplated, one preferred linker includes a linker that is cleavable in a mild acidic environment (e.g., at a pH between 3-6, at a pH between 4-6, at a pH between 4.5-5.5, etc.), yet stable in a neutral pH. For example, preferred acid-labile linkers include a thimaleamic acid linker and an acid-cleavable hydrazine linker (e.g., hydrazine linker, etc.).

In another aspect of the inventive subject matter, the inventors contemplate that a recombinant expression vector including a nucleic acid sequence that encodes a hypo-glycosylated mutant form of B7-H4, as described above, can be generated to so deliver the recombinant nucleic acid to the antigen-presenting cells (e.g., dendritic cells, APCs, tumor cell, etc.), for example, via viral transfection or DNA vaccine. As will be readily appreciated, any suitable expression vectors can be used that is suitable for recombinant protein expression.

Thus, in one embodiment, the microorganism is a virus, and a preferred expression vector includes a viral vector (e.g., nonreplicating recombinant adenovirus genome, optionally with a deleted or non-functional E1 and/or E2b gene). In still further embodiments, the microorganism is a bacteria, and the expression vector can be a bacterial vector that can be expressed in a genetically-engineered bacterium, which expresses endotoxins at a level low enough not to cause an endotoxic response in human cells and/or insufficient to induce a CD-14 mediated sepsis when introduced to the human body. One exemplary bacteria strain with modified lipopolysaccharides includes ClearColi® BL21(DE3) electrocompetent cells. This bacteria strain is BL21 with a genotype F-ompT hsdSB (rB- mB-) gal dcm lon λ(DE3 [lacI lacUV5-T7 gene 1 indl sam7 nin5]) msbA148⊿gutQ ⊿kdsD ⊿lpxL⊿lpxM⊿pagP⊿lpxP⊿leptA. In this context, it should be appreciated that several specific deletion mutations (ΔgutQ ΔkdsD ΔlpxL ΔlpxMΔpagPΔlpxPΔeptΔ) encode the modification of LPS to Lipid $IV_A$, while one additional compensating mutation (msbA148) enables the cells to maintain viability in the presence of the LPS precursor lipid IVA. These mutations result in the deletion of the oligosaccharide chain from the LPS. More specifically, two of the six acyl chains are deleted. The six acyl chains of the LPS are the trigger which is recognized by the Toll-like receptor 4 (TLR4) in complex with myeloid differentiation factor 2 (MD-2), causing activation of NF-κB and production of proinflammatory cytokines. Lipid $IV_A$, which contains only four acyl chains, is not recognized by TLR4 and thus does not trigger the endotoxic response. While electrocompetent BL21 bacteria is provided as an example, the inventors contemplates that the genetically modified bacteria can be also chemically competent bacteria. Alternatively, or additionally, the microorganism is a yeast, and the expression vector can also be a yeast vector that can be expressed in yeast, preferably, in *Saccharomyces cerevisiae* (e.g., GI-400 series recombinant immunotherapeutic yeast strains, etc.).

It is contemplated that such prepared or generated pharmaceutical composition and/or the tumor vaccine (including or containing the expression vector encoding a hypo-glycosylated mutant form of B7-H4) can be administered to a patient having a tumor to increase effectiveness of immune therapy to so treat the tumor (e.g., to modulate (e.g., reduce, abrogate, etc.) immune suppression by the tumor, to reduce the tumor size, etc.). In some embodiments, pharmaceutical composition and/or the tumor vaccine can be administered via systemic injection including subcutaneous, subdermal injection, or intravenous injection. In other embodiments, where the systemic injection may not be efficient (e.g., for brain tumors, etc.) or more localized treatment is desired, it is contemplated that the recombinant immunoglobulin protein complex and/or pharmaceutical compositions can be administered via intratumoral injection. As used herein, the term "administering" refers to both direct and indirect administration of the compounds and compositions contemplated herein, where direct administration is typically performed by a health care professional (e.g., physician, nurse, etc.), while indirect administration typically includes a step of providing or making the compounds and compositions available to the health care professional for direct administration.

With respect to dose and schedule of the administration, it is contemplated that the dose and/or schedule may vary depending on depending on the type of protein, protein complex, or the type of the pharmaceutical composition (e.g., virus, bacteria, yeast, in combination with recombinant protein complex, etc.), type and prognosis of disease (e.g., tumor type, size, location), health status of the patient (e.g., including age, gender, etc.). While it may vary, the dose and schedule may be selected and regulated such that the formulation does not provide any significant toxic effect to the host normal cells, yet sufficient to be reduce immune suppression by reduced T cell differentiation and/or activation in the tumor microenvironment. Thus, in a preferred embodiment, an optimal or desired condition of administering the formulation can be determined based on a predetermined threshold. For example, the predetermined threshold may be a predetermined local or systemic concentration of T-cell activating, or T-cell released cytokines (e.g., IL-2, IL-12, IFN-γ, IL-12, IL-23, IL-1b, IL-6, or TGF-β, etc.) in the tumor microenvironment. Therefore, administration conditions are typically adjusted to have one or more of those cytokines increased in the tumor microenvironment at least 20%, at least 30%, at least 50%, at least 60%, at least 70% at least for 24 hours, 48 hours, 72 hours, 7 days, etc. Moreover, it is contemplated that the compounds and compositions presented herein may be co-administered (contemporaneously or sequentially) with NK cells. For example, suitable NK cells include autologous NK cells as well as NK92 cells and derivatives thereof (e.g., aNK cells, haNK cells, taNK cells, al commercially available from NantKwest, 9920 Jefferson Blvd. Culver City, Calif. 90232).

Without wishing to be bound by a specific theory, the inventors contemplate that introduction of a hypo-glycosylated mutant form of B7-H4 into the tumor microenvironment, as a free-floating form bound to a molecular carrier or as a surface-expressed form on the antigen presenting cells (e.g., dendritic cells, tumor cells, etc.) can competitively bind to a T cell molecule binding to B7-H4 such that the inhibitory effect of endogenous, tumor-cell expressed, and/or wild-type B7-H4 to the T cell differentiation and activation can be mitigated. Such mitigating effect of hypo-glycosylated mutant form of B7-H4 can be also via dimerization with endogenous, tumor-cell expressed, and/or wild-type B7-H4 to suppress the activity of the wild-type B7-H4.

Domain Specific Binding Motifs to B7-H4:

Both B7-H4 Ig-Like Domains Can Independently Bind to T Cells and Modulate Their Activation: Ig-like domains are present in diverses group of immune receptor and ligand families performing essential roles in antigen recognition, cell-cell interaction and protein stability. To check the functional role of each Ig-like domain in B7-H4, the inventors investigated the ability to provide independently co-inhibitory signals. IgV-like domain (IgV) and IgC-like domain (IgC) were cloned as soluble B7-H4 domains and purified as described above (as shown in FIG. 8). Analysis of these proteins showed that both Ig-like domains can form oligomers but the oligomerization state seemed to be more preferable for the IgC domain (see FIG. 8). The inventors then tested the capability of these B7-H4 domains, individually or combined, to bind to T cells. Interestingly, both IgV and IgC domains were retained independently and non-competitively, indicating the presence of two different receptors for B7-H4 on the surface of activated T cells (see FIG. 8).

Figure 8:
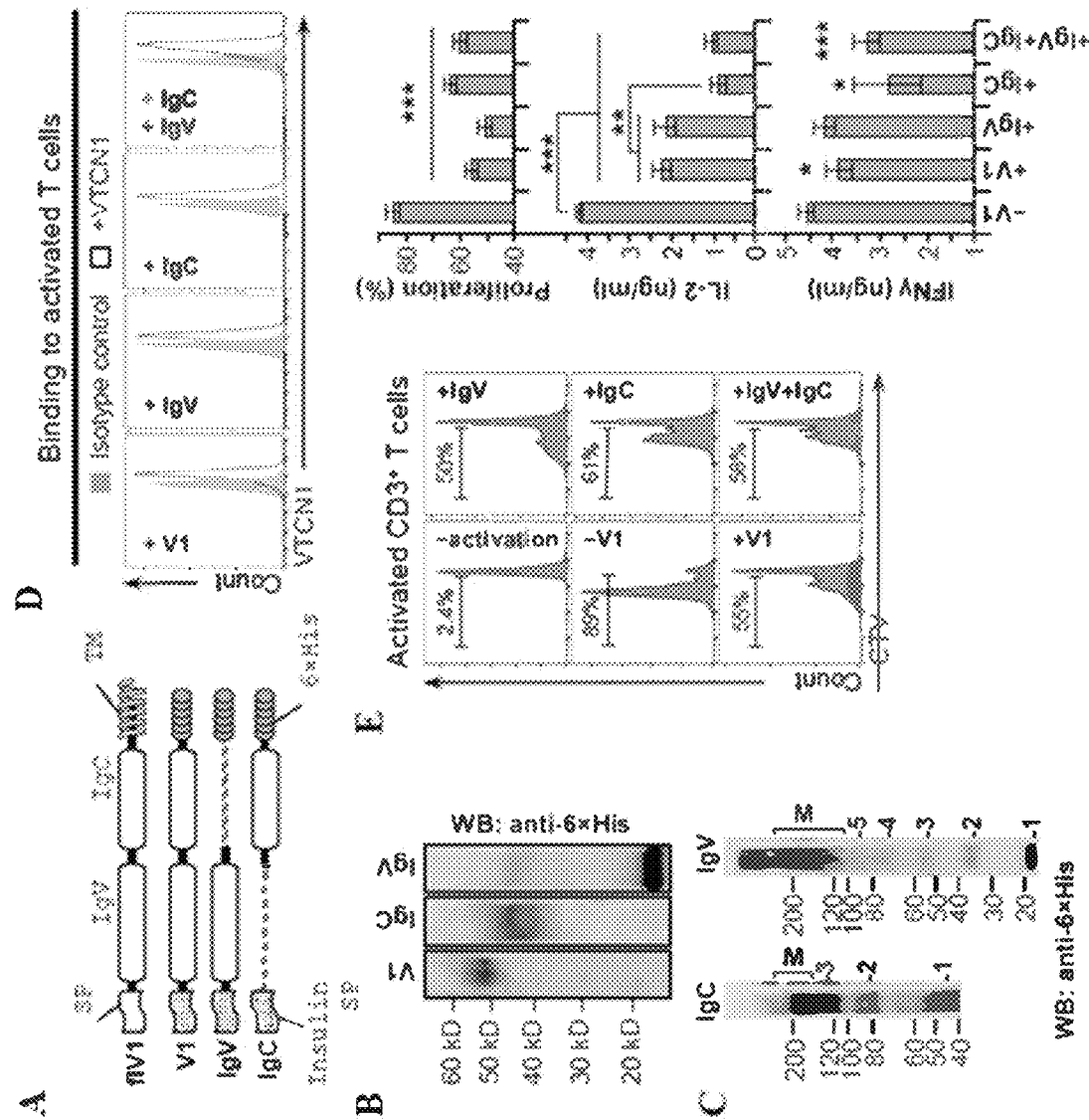
FIG. 8 shows western blotting and FACS analysis evidencing that individual IgC and IgV domains of B7-H4 can reduce T cell activation. (A) Schematic representation of generated soluble 6×His-tagged B7-H4 (V1), B7-H4's IgV (IgV) and B7-H4's IgC (IgC) constructs. (B) Western blot of V1, IgV and IgC proteins isolated from conditioned media of HEK cells stably expressing the indicated mutant construct. (C) Western blots analysis of IgV and IgC dimerization (as described for FIG. 1C). (D) FACS analysis of IgV and IgC binding to T cells (as described for FIG. 1E). Black line—anti-His; Gray shade—isotype control. (E) Left histograms—FACS analysis of CD3+T cell proliferation in the presence of V1, IgV, IgC and IgV+IgC (as described in FIG. 1B); CTV–Cell Trace Violet. Right bar graphs —quantification of proliferation and ELISA analysis of IFNT and IL-2 secreted by activated T cells. Data are represented as mean±SEM (n=6). *p<0.05; p<0.01; *p<0.001.

The inventors next examined which Ig-like domain of B7-H4 is responsible for the protein's biological activity, namely suppression of T cell proliferation and control of the pro-inflammatory cytokines production. For this, isolated murine CD3$^+$T cells were labeled with CFSE, pre-treated with recombinant proteins, and then activated for 5 days with CD3 and CD28 antibodies at which time point the proliferation of T cells was analyzed (FIG. 8, left histograms).

The inventors found that the IgV inhibitory activity on proliferation of CD3$^+$T cells was similar to this of V1. However, IgC was also capable to suppress T cells proliferation ($p<0.001$), even though to a lesser extent than V1. Additionally, the IgC treatment reduced IFNγ and IL-2 levels more than V1 or IgV (as shown in FIG. 8, right bar graphs). When combined at 1:1 molar ratio, IgV+IgC had a mixed effect represented by a stronger than IgC alone inhibition of T cell proliferation combined with low IL-2 and IFNγ levels resembling the IgC treatment (as shown in FIG. 8). These results additionally support the assumption that there are two independent receptors for B7-H4 Ig-like domains pointing towards the possibility that IgC and IgV independently trigger different inhibitory pathways ultimately resulting in reduction of T cell activation.

Figure 9:
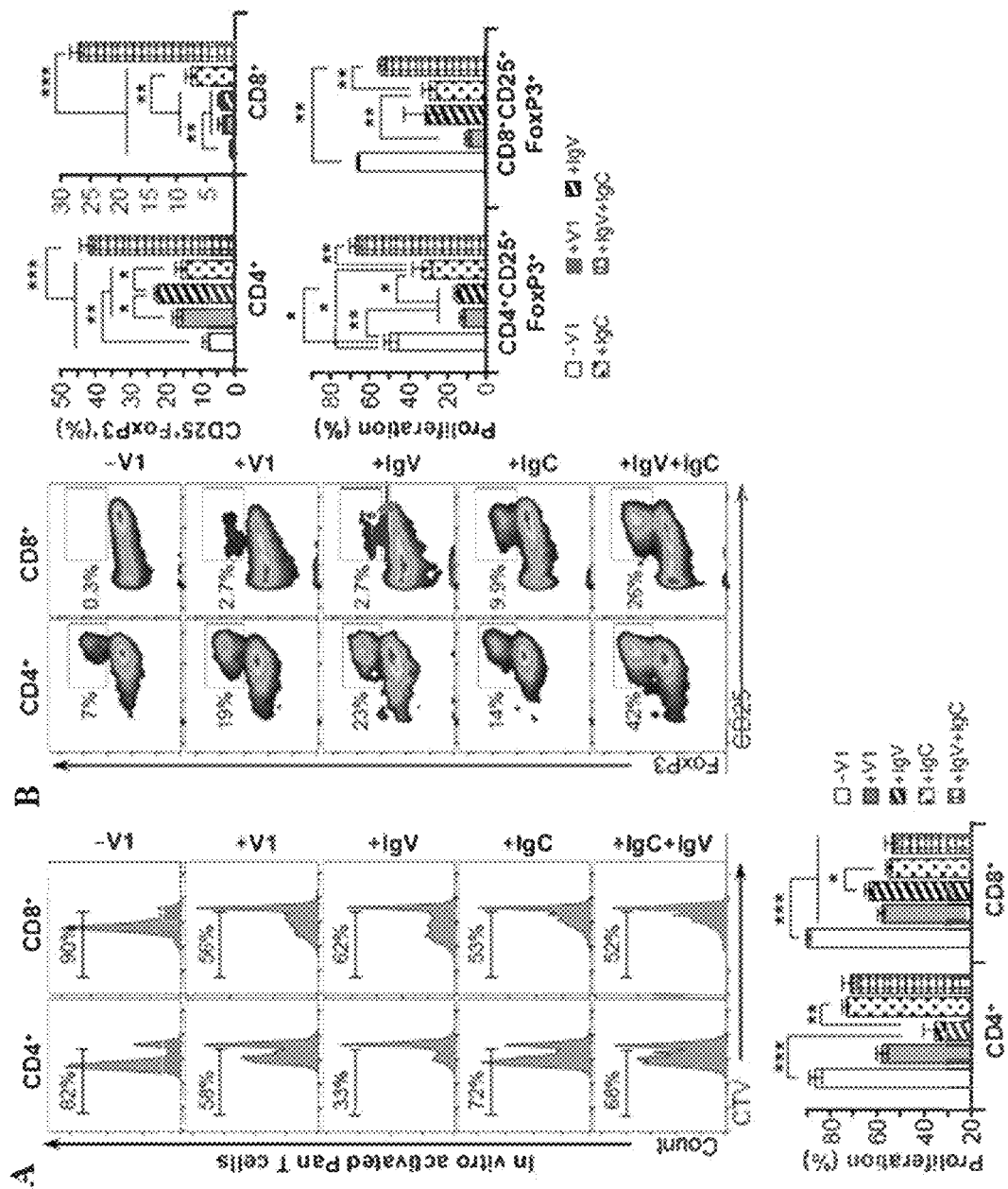
FIG. 9 shows FACS analysis evidencing that B7-H4 IgV-like domain has higher specificity for CD4* while B7-H4 IgC-like domain inhibits more efficiently CD8+T cells. (A) FACS analysis of the proliferation status of CD4$^+$ and CD8$^+$T cells after anti-CD3/anti-CD28 activation of Pan T cells in the presence of the indicated protein. Lower bar graph —quantification of the percentages of proliferating T cells. (B) Left histograms—Representative FACS analysis of CD4$^+$CD25$^+$FoxP3$^+$ and CD8$^+$CD25$^+$FoxP3$^+$ after treatment of pan T cells with the indicated protein. See also Figures S3 and S5. Right bar graphs—Quantification of Tregs and their proliferation. Data are represented as mean±SEM (n=6). *p≤0.05; p-0.01; *p≤0.001.

B7-H4's IgV- and IgC-Like Domains Exert Different Degree of Suppression of Various T Cells' Subsets: One possible explanation for the discrepancies between the proliferation and cytokine secretion observed after IgV and IgC treatment of Pan T cells is that these domains are targeting different T cell subsets. The inventors therefore analyzed the proliferation of CD4$^+$ and CD8$^+$ within the total live CD3$^+$T cell population (as shown in FIG. 9). The inventors found that IgV is considerably better suppressor of CD4$^+$T cell's proliferation than V1, IgC or IgV+IgC. At the same time, IgC was more potent than IgV in suppressing CD8$^+$ cells, implicating a separated specificity of these domains for CD4$^+$ and CD8$^+$T cells. Furthermore, even though IgV+IgC closely resembled the effect of IgC, the V1 was acting more like IgV in suppressing CD4$^+$ and CD8$^+$T cells showing that the separation of the two Ig-like domains possibly unlock additional activities that are subdued in the whole B7-H4 molecule. The later observation of IgC-mediated abrogation of cytokine levels hinted that the detected phenomenon might depend not only on reduced cytokines synthesis/release, but also on enhanced utilization of the released cytokines. Since T regulatory cells are known to be the main IL-2 consuming cell population, the inventors analyzed the effects of individual B7-H4 domains on the state of Tregs in vitro. Remarkably, the treatment of activated CD3$^+$T cells with tested B7-H4 or with its individual IgV and IgC domains, increased the percentages of both CD4$^+$CD25$^+$FoxP3$^+$T cells, with the IgV+IgC treatment providing the most pronounced increase (as shown in FIG. 9, left row). At the same time, the number of Tregs before and after activation in the absence of recombinant proteins was not significantly affected (see FIG. 16). Surprisingly, this effect was not restricted only to the classical Tregs (CD4$^+$) as similar result was also observed with the non-canonical CD8$^+$CD25$^+$FoxP3$^+$ cells, an important subset of T suppressors capable to inhibit T-cell responses in autoimmunity and alloimmunity. Additionally, the IgC domain of B7-H4 had affected more prominently CD8$^+$Tregs compared to IgV, which in turn was more specific for the CD4$^+$Tregs (FIG. 9, right row). Interestingly, when the inventors analyzed the proliferation of CD4$^+$FoxP3$^+$CD25$^+$T cells, the inventors found that unlike the other proteins, IgV+IgC mixture treatment led to a robust proliferation of all Tregs-like cells confirming the previous conclusion that the separation of Ig-like domains enhanced their activity.

De Novo Induction of Functional CD4$^+$CD25$^+$FoxP3$^+$ Tregs-Like Cells By B7-H4 IgC Domain: The elevated Tregs numbers after IgV+IgC treatment could be due to a higher propagation/stability of pre-existing Tregs or a result of de novo induction of Tregs from naïve CD4$^+$T cell. Since the inventors were using Pan T cells in the experiments, the inventors could not discriminate between those two possibilities. Therefore, the inventors next examined the ability of B7-H4 domains to induce expression of CD25$^+$ and FoxP3$^+$ in naïve CD4$^+$CD25– and CD8$^+$CD25– T cells. For this, murine naïve CD4$^+$ and CD8$^+$T cells were activated in the presence/absence of recombinant proteins as described above. The results showed that more naïve T cells acquired Treg phenotype when treated with IgC domain as IgV+IgC had the most prominent effect indicating that the IgC domain is the main driving factor for Treg conversion (see FIG. 10). It is known that TGFβ is crucial for the induction and stability of Tregs.

Therefore, the inventors analyzed the amounts of TGFβ in media collected at the end of this experiment. Consistently with the observed Treg numbers, IgC and IgV+IgC treatments elevated TGFβ levels providing evidence that the mechanism of IgC action is probably through stimulation of TGFβ expression (see FIG. 10).

Figure 10:
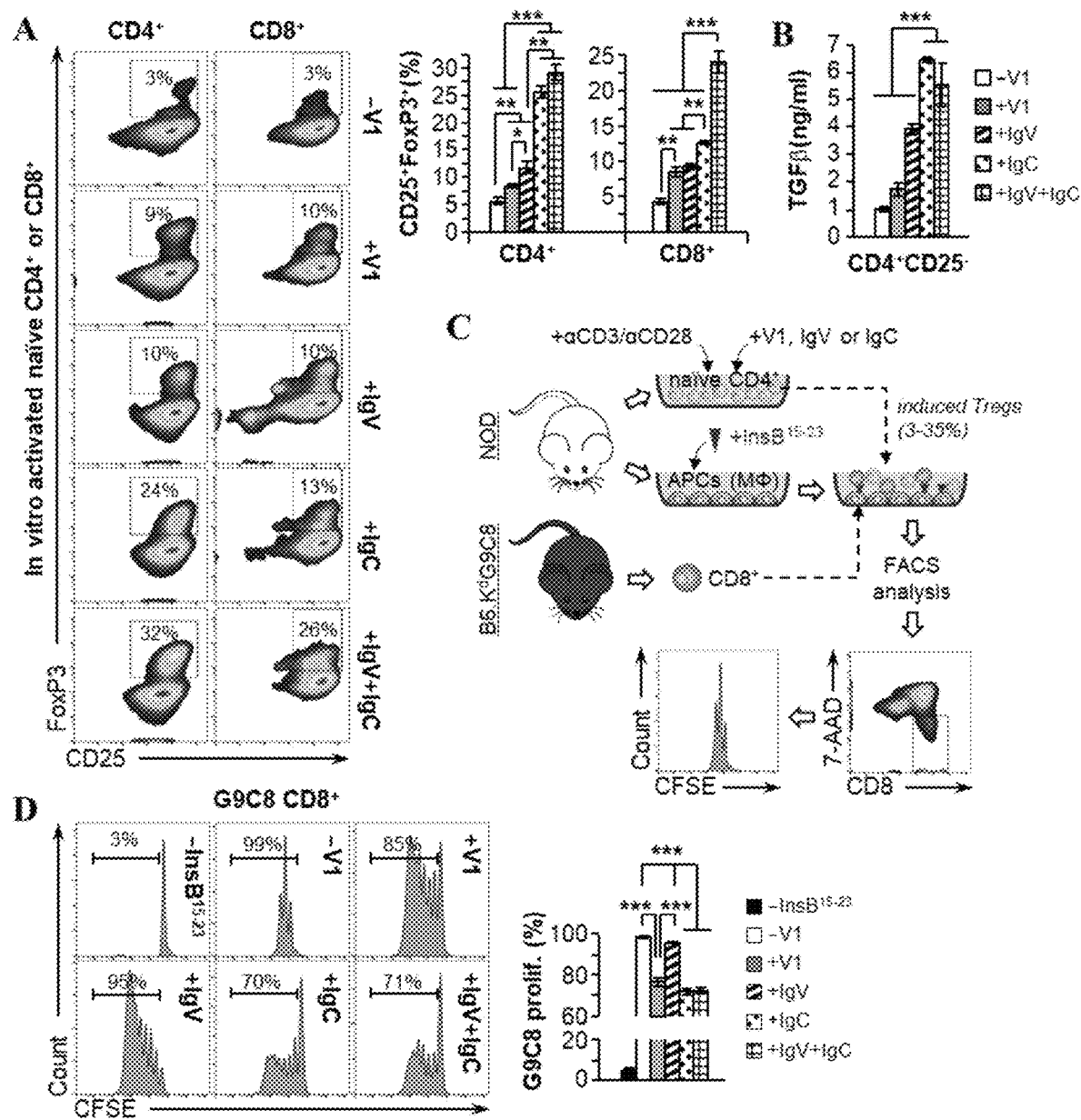
FIG. 10 shows FACS assay and the bar graphs of FACS assay results evidencing that B7-H4 IgC-like domain stimulates the conversion of naïve T cells into functional Tregs. A) Naïve CD4$^+$CD25$^-$ and CD8$^+$CD25$^-$T cells were isolated from mouse spleen, activated in the presence of the indicated recombinant protein and then analyzed by FACS for the presence of CD25$^+$FoxP3$^+$ cells. Right bar graph—Quantification of Tregs. (B) ELISA for TGFβ of conditioned media collected from the experiment shown in (A). (C) Outline of the suppression assay with classical Tregs. First, naïve T cells were activated for 5 days in the presence of indicated recombinant protein (as described in FIG. 5A). Next, insulin peptide-loaded macrophages were co-cultured for 6 days with 1:1 ratio of CFSE-labeled G9C8 CD8+ cells and the activated naïve CD4+ cells. At the end, these co-cultures were gated for the live CD8+ cells and their proliferation was analyzed. (D) Left histograms—Representative FACS of G9C8 CD8+T cell proliferation. Right bar graph—quantitative analysis. Data are represented as mean±SEM (n=6). *p≤0.05; p≤0.01; *p≤0.001.

To understand if converted Treg-like cells are functional and could regulate the activation of effector T cells (Teffs cells), the inventors used them in a suppression assay with diabetogenic G9C8 CD8$^+$T cells (as Teffs) and insulin peptide-loaded macrophages (as feeder cells) as is shown in the schematic illustration of FIG. 10. For this assay, NOD macrophages were co-cultured with CFSE labeled G9C8 T cell and pre-activated naïve T cells. Strikingly, a significantly decreased proliferation of G9C8 cells was observed in co-cultures with IgC- or IgV+IgC-treated naïve CD4+T cells but not with IgV- or V1-treated, showing that only IgC-induced Treg cells are the most functionally proficient (see FIG. 10).

Figure 11:
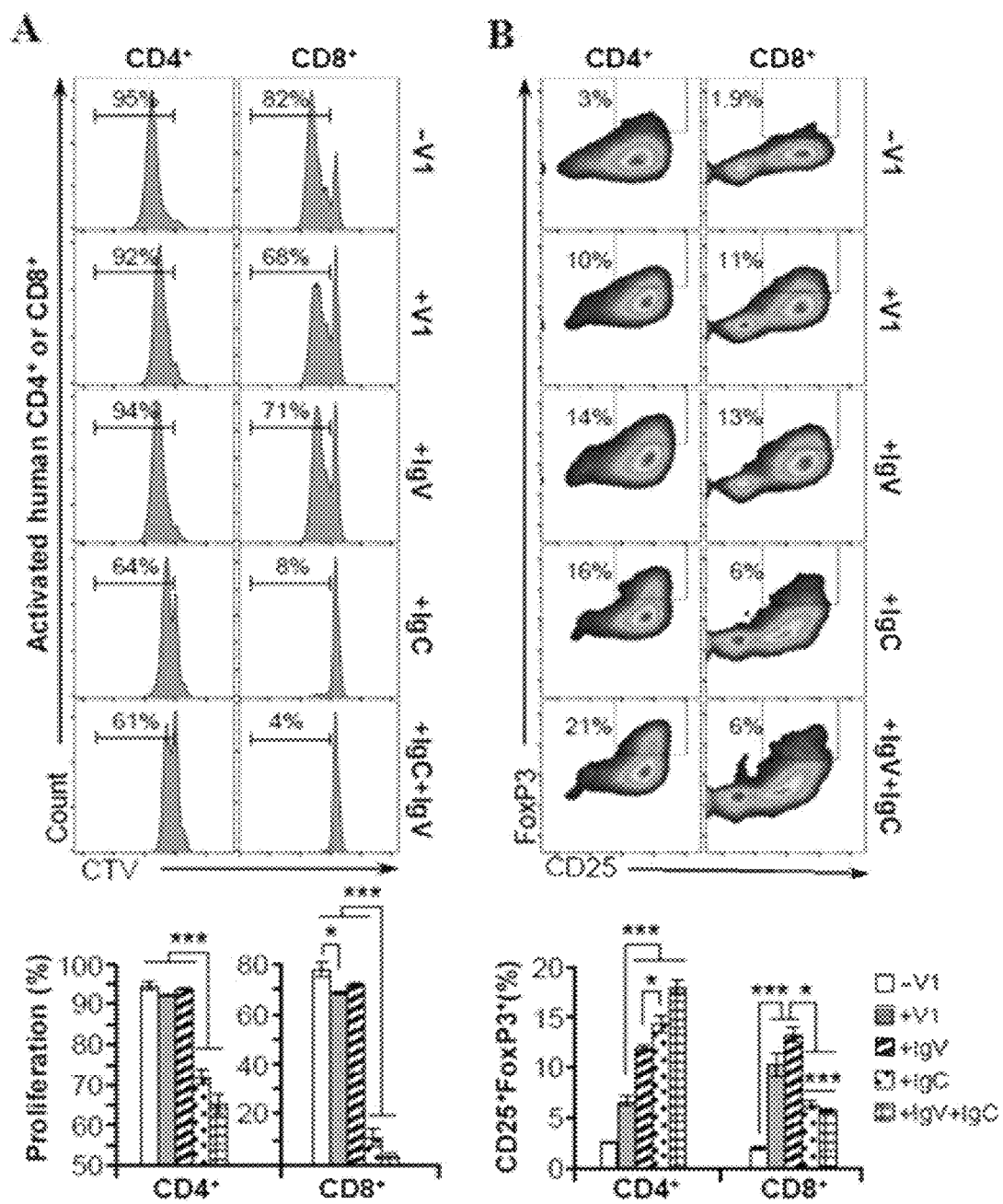
FIG. 11 shows FACS analysis and graphs of FACS assay results evidencing that B7-H4 IgC domain is highly specific for human T cells' activation and Treg conversion. (A) Top—FACS analysis of the proliferation of human CD4+ and CD8+T cells in the presence of V1, IgV, IgC and IgV+IgC (as described in FIG. 1). Bottom—quantification of the percentages of proliferating T cells. (B) Top—Representative FACS analysis of CD4+CD25+FoxP3+ and CD8+CD25+FoxP3+after treatment of human CD4+ or CD8+T cells with the indicated protein. Bottom—Quantification of Tregs numbers. Data are represented as mean±SEM (n=3). *p≤0.05; p≤0.01; *p≤0.001.

Mouse B7-H4's IgV- and IgC-domains Stimulate Tregs Conversion of Human T cells: It is well-known that mouse and human Tregs have some differences that may present obstacles transferring the inventors' data from mouse models to humans. In humans, unlike mice where Tregs are homogenous and virtually all CD4+CD25+ cells are FoxP3+, Tregs are more heterogeneous. Only 2-3% of the total human CD4+ cells have regulatory functions as they are characterizing with very high levels of CD25. Therefore, the inventors next tested if V1 and its domains also affect human T cells. For this purpose, commercially obtained human CD4+ and CD8+T cells were activated in the presence of IgV, IgC or IgV+IgC and then analyzed by FACS (see FIG. 11). Some notable differences from the mouse T cells were observed, as the IgC domain was much more potent in inhibiting both CD4+ and CD8+T cell proliferation than IgV or V1 (see FIG. 11). Furthermore, even though the CD4+ Treg population was mostly increased by the presence of IgC (similarly to mouse), the IgV appeared to be much stronger initiator of CD8+CD25+FoxP3+ cells (see FIG. 11).

In view of the above, it should therefore be recognized that the inventors identified the presence of at least two distinct receptors or receptor domains for B7-H4: one for each Ig-like domain, which is also consistent with the ability of B7-H4 to deliver two diverse effects: Inhibition of Teffs cells and stimulation of regulatory T cells. Confirming previous conclusions that IgV mediates the activity of B7-H4 activity, the full-length B7-H4 and IgV alone had similar functional characteristics (see FIGS. 8, 9, 10). At the same time, a combination of IgV+IgC provides synergistic effects of IgV and IgC in regulating T cell suppression, showing that the IgC domain is not completely active when linked to IgV in the whole B7-H4 form, most probably due to spatial/conformational reasons or differential specificity of the receptor. Recent reports revealed the crystal structure of the IgV domain of human B7-H4, suggesting the IgV domain to be receptor-binding/functional part of B7-H4. This conclusion was supported by the fact that the 1H3 monoclonal antibody that strongly interacts with IgV domain of B7-H4 partially blocked B7-H4-induced T cell suppression in experiments with in vitro T cell activation. The inability of the antibody to completely block B7-H4 inhibitory action along with the inventors' results show the possibility that the IgC domain of B7-H4 by itself is functionally active, exerting some degree of negative co-stimulation when IgV domain is blocked. Here, the inventors discovered that both B7-H4 domains independently and non-competitively bind to activated T cells, a conclusion based on the fact that IgV+IgC signal intensity was higher than the one with B7-H4 or individual domains (see FIG. 8). Moreover, the inventors' data revealed that IgV and IgC domains of B7-H4 possess negative co-stimulatory functions, targeting different T cell subsets and imparting suppressive effects in distinct ways.

The inventors' data with pan T cells also showed that B7-H4 along with each of its individual domains is capable to increase the frequencies of T cells in vitro. However, IgC domain treatment led to higher reduction of IL-2 levels (see FIG. 8). This suggested that the number of IgC-mediated Tregs is higher or they are better functioning thus consuming more IL-2. Indeed, IgC treatment enhanced de novo induction of CD4+CD25+Tregs from naïve CD4+T cells that are able to moderate the activation of diabetogenic G9C8 CD8+T cell clones (see FIG. 5). At present, exogenous supplementation of IL-2 and TGFβ is thought to be crucial to convert naïve CD4+T cells into Tregs cells, with TGFβ signaling leading to FoxP3 expression. This conclusion is supported in the inventors' data where IgC treatment resulted in increased secretion of TGFβ in cultures of activating naïve T cells (FIG. 10), which clearly shows that this domain has the potential to induce secretion of TGFβ which in turn is utilized to convert T cells into Tregs, most probably via phosphorylation of SMADs. Most importantly, the IgC domain converts naïve CD4+T cells into functional Tregs unlike the IgV domain (albeit the appearance of some Treg-like cells) (see FIG. 10). This explains why the IgC+IgV treatment, which generated the highest number of Treg-like cells (corresponding to the sum of individual domains) had the same effect in suppression assay as B7-H4 or IgC alone (see FIG. 10). This also shows that the Treg-like cells converted by the IgV domain are incapable to regulate the activities of Teffs cells.

In still further experiments, the inventors investigated the conversion of naïve CD4+T cells isolated from NOD-FOXP3. More specifically, naïve CD4+CD25– T cells were isolated from spleens of NOD-FOXP3. EGFP mice and then activated with anti-CD3/CD28 microbeads in the presence or absence of the indicated recombinant molecule as indicated. After 5 days of activation, the cells were collected and analyzed for EGFP expression by FACS. As can be seen from the results in FIG. 17, the conversion efficiency using the IgC domain and a combination of separate IgC and IgV domains was substantially higher than using IgV and construct V1.

Changes in FoxP3 transcription were investigated using various constructs as is shown in FIG. 18. Here, naïve CD8+CD25– T cells were activated with anti-CD3/CD28 microbeads in the presence or absence of the indicated recombinant protein. After 72 hours, cells were collected, total RNA was isolated and then used for RT qPCR. As a control, freshly isolated naïve CD8+T cells were used. Panel A depicts changes in Foxp3 gene expression levels, while Panel B shows a comparison of Foxp3 expression levels in converted CD8+Tregs with freshly isolated classical CD4+ Treg cells. Panel C shows a comparison of the CD8 expression in activated naïve CD8+cells to activated naïve CD4+ cells.

Experimental Procedures

Mice: Female NOD/ShiLtJ (NOD) mice were from The Jackson Laboratory.

B6.K$^d$G9C8 mice, transgenic for TCR derived from InsB$^{15-23}$-specific CD8+T cell clone G9C8, and H-2K$^d$ MHC allele were provided by Dr. A. Chervonsky (University of Chicago). All mice were maintained in the animal facility according to the NIH guidelines for animal use.

Cloning and expression of soluble B7-H4: The extracellular portion of B7-H4 fused to a 6×His-tag was cloned and then used for generation of all other mutant proteins following standard protocols. HEK cells transiently or stably transfected with these constructs were used for all experiments.

Protein purification and dimerization: The recombinant proteins were affinity purified from conditioned medium by Ni-NTA agarose (Invitrogen). Deglycosylated B7-H4 was purified in denaturing conditions and then buffer exchanged since it was retained on the Ni-NTA column in physiological buffer. For the dimerization studies, proteins were incubated with BS$^3$ (0.5 mM) in PBS for 30 mins at 4° C. and then reactions were quenched with 30 mM Tris-HCl pH 7.5 and analyzed by western blot.

Immune cells isolation and proliferation assay: Residential peritoneal macrophages from NOD mice were prepared as described (Radichev et al., 2014). T cells were labeled with CFSE or Cell Trace Violet and activated with anti-CD3 and anti-CD28 antibodies for 5 days, in the presence or absence of recombinant protein (180 nM). Conditioned media for ELISA was collected on day 3. T cell proliferation was analyzed by FACS.

Binding assay: Pre-activated T cells were incubated with B7-H4 recombinant protein and binding was evaluated after staining with anti-6×His-FITC on an Accuri C6 Flow Cytometer.

Deglycosylation and half-life analysis of B7-H4: Peritoneal macrophages or HEK cells expressing full length B7-H4 were treated for 16 hrs with 5 µg/ml of tunicamycin (Sigma-Aldrich) and then either fixed for immunofluorescence or lysed for immunoblotting. Deglycosylation of purified B7-H4 (1-5 µg) was performed by treatment with 0.5 µl of PNGase F (Promega) for two hours at 37° C. To analyze the half-life of recombinant proteins, HEK cells were transfected with V1, M1, M2 or M8 constructs. 24 hours post-transfection, the medium was replaced and 10 µg/ml cycloheximide (Sigma) or vehicle was added to the cells. Cells were then incubated for the indicated time before western blot analysis.

In Vitro Tregs Induction and Suppressor Assays: Naïve CD4$^+$CD25− and CD8$^+$CD25− T cells were labeled with CFSE and after short incubation with the indicated recombinant protein were activated for 5 days with Dynabeads Mouse T-Activator CD3/CD28. The cells were then stained with a viability marker, anti-CD4/CD8, anti-CD25 and anti-FoxP3 (all eBioscience) and analyzed by FACS. For suppressor assay, activated naïve CD4$^+$CD25− T cells were co-cultured with insulin peptide-loaded macrophages and CFSE-labeled, insulin-specific B6.G9C8 CD8$^+$T cells. At the end, cells were stained with 7AAD (for viability) and anti-CD8 and analyzed for proliferation on Accuri C6 Flow Cytometer. Human CD4$^+$ and CD8$^+$ cells were obtained by StemCell Technologies (Vancouver, Canada) and activated for 5 days with 25 µl/ml of ImmunoCult Human CD3/CD28 T Cell Activator in ImmunoCult-XF T cell expansion medium (all from StemCell Technologies) in the presence or absence of recombinant protein.

FACS analysis: Single-cell suspensions in FACS buffer (0.5% BSA in PBS) were blocked with Fc-receptor antibodies (eBioscience) and after staining with the specified antibodies were ran on Accuri-C6 or LSRFortessa (BD Biosciences) instrument and then analyzed with FlowJo (FlowJo LLC) software. The gating strategies are shown on FIGS. 14A-D. Here, (A) cells (excluding the beads in experiments where T cells were activated with anti CD3/CD28 Dyna beads) were gated, and live CD4+ T cells were selected. Next, gated cells were analyzed either for proliferation or Treg population based on CD25 and FoxP3 positivity. (B) Gating strategy for identification of CD8+ Tregs. Cells were gated similarly to (A). (C) Gating strategy for human CD4+ Tregs. (D) Gating strategy for human CD8+ Tregs.

ELISA: Conditioned media was analyzed for IL-2 and INF7 using mouse ELISA-construction kits (eBioscience) following manufacturer's recommendations. TGFβ was measured with Mouse/Rat/Porcine/Canine TGF-01 Quantikine ELISA kit (R&D Systems).

Western blot: RIPA-cell lysates and concentrated in Amicon Ultra-1OK concentrators (Millipore) serum-free media were subjected to western blot analysis with a HRP-chemiluminescent detection system. The blots were scanned on UVP BioSpectrum 500 imaging system.

Immunofluorescence: Macrophages and HEK cells were fixed in 4% PFA and then processed for intracellular staining (after permeabilization) or for cell surface staining (no permeabilization). Cells were stained for B7-H4 and calnexin and observed under a Nikon-A1 microscope.

Statistics: Unpaired Student's t-test was performed using GraphPad Prism (GraphPad Software).

Thus, the inventors contemplated that the effectiveness of immune therapy in the patient having a tumor can be increased with a recombinant protein complex that has two binding motifs: a first binding motif to IgC portion of B7H4 and a second binding motif to IgV portion of B7H4. While any suitable portion(s) for the first and second binding motifs in B7H4 are contemplated, it is preferred that the target portion(s) of the B7H4 for the first and second binding motifs are selected to 1) allow the first and second binding motifs can be bound to the B7H4 molecule in vivo concurrently and/or simultaneously, and 2) effectively hinder/interfere the function of the B7H4 by IgC portion and IgV portion, respectively. Thus, such binding motifs can be generated using at least 30%, at least 50%, at least 70%, or a whole IgC portion or IgV portion as epitopes.

Any suitable forms of binding motifs (affinity portion) that can act alone and/or coupled to another peptide/non-peptide backbone (e.g., IL-15Ra of TxM) are contemplated. Preferred binding motif includes a whole antibody (e.g., IgG, IgM, IgE, and IgA), a portion of an antibody (e.g., one or more Fab, Fab', F(ab)$_2$, etc.), or single chain variable fragment (scFv). Alternatively, suitable affinity portions may also include proteins that were obtained by affinity maturation (e.g., using phage display) or by RNA display.

In some embodiments, the two binding motifs (one to IgC portion and another to IgV portion) can be coupled together via a linker, and optionally further coupled to a molecular carrier. The linker can be a non-cleavable linker that is typically between 3-30 amino acids, preferably between 5-20 amino acids, more preferably between 5-15 amino acids. Preferably, such linker is glycine-rich sequences (e.g., gly-gly-ser-gly-gly, etc.) to provide structural flexibility between the cytokine binding domain (or cytokine) with the extracellular portion of a hypo-glycosylated mutant form of B7-H4. Alternatively, the linker can be a linker that can be preferably cleaved in the tumor microenvironment. While any suitable linkers that can be preferentially cleaved in the tumor microenvironment and/or upon activation of immune system are contemplated, one preferred linker includes a linker that is cleavable in a mild acidic environment (e.g., at a pH between 3-6, at a pH between 4-6, at a pH between 4.5-5.5, etc.), yet stable in a neutral pH. For example, preferred acid-labile linkers include a thimaleamic acid linker and an acid-cleavable hydrazine linker (e.g., hydrazine linker, etc.).

With respect to the molecular carrier, one exemplary molecular carrier includes a nano particle to which the recombinant proteins can be directly or indirectly linked. The nano particle can be a bead, a nanoparticle, or a protein molecule that can be conjugated (or linked) with the one or more binding motifs. For example, the nano particle may include, but not limited to, protein A, protein G, protein Z, albumin, and refolded albumin. Especially, where the carrier protein is an albumin, the hydrophobic portion of one or more binding motifs may fit in one of Sudlow's site I and II of the albumin or any other hydrophobic area of the albumin. In some embodiments where the one or more binding motifs are not hydrophobic enough, it is contemplated that the recombinant peptide can be coupled with an hydrophobic short anchor peptide (in a length of at least 10 amino acids, 15 amino acids, 20 amino acids, 30 amino acids, etc.) such that the one or more binding motifs can be placed at the Sudlow's site I and II of the albumin via the hydrophobic short anchor peptide.

In some embodiments where the two binding motifs are coupled to the molecular carrier via an anchor peptide, it is contemplated that the anchor peptide comprises a dendrimer-type linker. Typically, a dendrimer-type linker includes a plurality of sublinkers that are connected to one support, where the support is coupled to the nano carrier (e.g., albumin, etc.). In such embodiment, at least two sublinkers may have different linker types such that the linkers can be cleaved or not cleaved in different conditions. For example, the linker may include a first acid-labile linker that is conjugated with the first binding motif to IgV domain of B7-H4, and further include a second glycine-rich non-cleavable linker that is conjugated with the first binding motif to IgC domain of B7-H4.

Alternatively, the two binding motifs can be coupled to an IL-15 superagonist (e.g., ALT-803 or TxM, etc.) via at least one of the cytokine-binding domain (IL-15R) or the cytokines (IL-15) associated with the cytokine-binding domain. For example, scFv to IgV domain of B7– H4 can be coupled to the cytokine-binding domain (IL-15R), optionally via a linker, and scFv to IgC domain of B7-H4 can be coupled to the cytokine (IL-15), also optionally via a linker. Additionally, at least one of the cytokine-binding domain or cytokine are linked to one of the binding motifs to B7-H4 via a dendrimer-type linker such that one of the binding motifs to B7– H4 and the binding motif to a tumor-associated antigen, preferably a patient-specific and/or tumor-specific neoepitope to target the IL-15 superagonist protein complex to the tumor microenvironment. For other example, an scFv to IgV domain of B7-H4 and an scFv to IgC domain of B7-H4 can be coupled to the cytokine-binding domain (IL-15R) via a dendrimer-type linker while a binding motif to a tumor-associated antigen can be coupled to the cytokine (IL-15). In those examples, the recombinant IL-15 superagonist complex can be targeted to the tumor microenvironment via the binding motif to a tumor-associated antigen such that the binding motifs to the B7-H4 can specifically target B7-H4 overexpressed on the tumor cells.

It is contemplated that such prepared or generated recombinant protein complex having two binding motifs to different portions of B7H4 can then be administered to the patient having a tumor to increase effectiveness of immune therapy to so treat the tumor (e.g., to modulate (e.g., reduce, abrogate, etc.) immune suppression by the tumor, to reduce the tumor size, etc.). Without wishing to be bound to any specific theory, the inventors contemplated that the recombinant protein complex will bind to IgC and IgV domain independently and concurrently such that the immune-suppressive activity via those domains can be suppressed, for example, suppressed $CD4^+T$ cell proliferation by IgV domain, suppressed $CD8^+$ cell proliferation by IgC domain, IgC domain-mediated abrogated cytokine level, enhanced activity of Treg cells, and stimulated Treg conversion from other types of T cells.

In still further contemplated aspects, functional testing of various forms of the BB7-H4 antibodies was performed to confirm specific binding to B7-H4, establish cytotoxicity on B7-H4 expressing cells, and cytotoxicity of CAR constructs with an antiB7-H4 ectodomain. More specifically, and as is shown in FIG. 19, a B7-H4 expressing cell line (MX-1) was first tested via FACS for surface expression of B7-H4. The upper left panel depicts unstained MX-1 cells, while the lower left panel depicts MX-1 cells with labeled antiB7-H4 IgG antibody, labeled non-specific IgG antibody, and control. As is readily apparent, MX-1 cells express B7-H4 on the cell surface. The cells were further exposed to varying quantities of antiB7-H4 IgG antibodies (801 and 807), and specific antibody binding had a dose response as the graph in FIG. 19 illustrates.

Specific anti-B7-H4 IgG antibody-mediated cell lysis of MX-1 cells was demonstrated by exposing the MX-1 cells to various antibodies, including anti-B7-H4 IgG antibodies. As can be seen from FIG. 20, trastuzumab and 801 and 817 antibodies bound to respective antigens (Her2 and B7-H4) and triggered ADCC as is evidence by the target specific lysis, while negative controls failed to produce significant lysis even at high effector to target ratios. Both 801 and 817 IgG antibodies exhibited dose response characteristics in haNK cell dependent antibody-mediated lysis as is shown in FIG. 21. NK-cell ADCC was also observed in cells expressing recombinant B7-H4 as is shown in FIG. 22.

Where scFv forms of 801 and 817 were used in an ectodomain of a chimeric antigen receptor expressed on haNK cells, both modified NK cells showed specific and effective cell lysis of MX-1 cells as is shown in FIG. 23. Notably, as CAR the 801 ectodomain was more active than the 817 ectodomain. However, the 8107 ectodomain was significantly more active than the mock control.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of reversing or reducing B7-H4-mediated immune suppression in a subject in need thereof, comprising:
    administering to the subject an isolated antibody or antigen binding fragment thereof to thereby reverse or reduce the B7-H4-mediated immune suppression in the subject;
    wherein the antibody or fragment binds to B7-H4, and wherein the antibody or fragment comprises $VH_{801}$ (SEQ ID NO:1) and $VL_{801}$ (SEQ ID NO:2) or $VH_{817}$ (SEQ ID NO:3) and $VL_{817}$ (SEQ ID NO:4).

2. The method of claim 1, wherein the $VH_{801}$ (SEQ ID NO:1) and the $VL_{801}$ (SEQ ID NO:2) or the $VH_{817}$ (SEQ ID NO:3) and $VL_{817}$ (SEQ ID NO:4) are coupled together by a linker to form an scFv.

3. The method of claim 1, wherein the antibody or antigen binding fragment thereof is an $IgG_1$ antibody or an scFv.

4. The method of claim 1, wherein the antibody or antigen binding fragment thereof further comprises a therapeutic agent.

5. The method of claim 4, wherein the therapeutic agent is a chemotherapeutic drug, a radionuclide, or an immune stimulant.

6. The method of claim 4, wherein the immune stimulant is a cytokine, a cytokine analog, a chemokine, or a checkpoint inhibitor.

7. The method of claim 1, wherein the antibody or antigen binding fragment comprises an additional peptide portion to thereby form a chimeric protein.

8. The method of claim 7, wherein the chimeric protein is configured as a chimeric antigen receptor.

9. The method of claim 8, wherein the chimeric antigen receptor is expressed on an NK cell or a cytotoxic T cell.

10. The method of claim 7, wherein the chimeric protein is configured as a bispecific fusion protein.

11. The method of claim 10, wherein the bispecific fusion protein comprises a IgG Fc portion, and optionally further comprises at least one of an IL15a receptor portion, an IL15 portion, and an IL15 superagonist portion.

12. The method of claim 7, wherein the chimeric protein is configured as a bispecific killer cell engager (BiKE) or a trispecific killer cell engager (TriKe).

13. The method of claim 1, wherein the subject in need thereof is has prostate cancer, ovarian cancer, breast cancer, pancreatic cancer, or renal cancer.

14. The method of claim 1, further comprising administering a cancer vaccine to the subject in need thereof.

15. The method of claim 1, wherein administration is subcutaneous injection, subdermal injection, intravenous injection, or intratumoral injection.

16. A pharmaceutical composition for immune therapy, comprising:
    a pharmaceutically acceptable carrier in combination with an isolated antibody or antigen binding fragment thereof, wherein the antibody or fragment binds to B7-H4, and
    wherein the antibody or fragment comprises $VH_{801}$ (SEQ ID NO:1) and $VL_{801}$ (SEQ ID NO:2) or $VH_{817}$ (SEQ ID NO:3) and $VL_{817}$ (SEQ ID NO:4).

17. The pharmaceutical composition of claim 16, wherein the antibody or antigen binding fragment thereof is an $IgG_1$ antibody or an scFv.

18. The pharmaceutical composition of claim 16, wherein the antibody or antigen binding fragment thereof further comprises a therapeutic agent selected from the group consisting of an immune stimulant, a chemotherapeutic drug, and a radionuclide.

19. The pharmaceutical composition of claim 16, wherein antigen binding fragment is part of a chimeric antigen receptor, and wherein the chimeric antigen receptor expressed on a cell surface of an NK cell or a T cell.

20. The pharmaceutical composition of claim 16, wherein the antibody or antigen binding fragment thereof is part of a bispecific fusion protein, a bispecific killer cell engager (BiKE), or a trispecific killer cell engager (TriKe).

* * * * *

SEQUENCE LISTING

```
<160> NUMBER OF SEQ ID NOS: 4

<210> SEQ ID NO 1
<211> LENGTH: 120
<212> TYPE: PRT
<213> ORGANISM: Artificial Sequence
<220> FEATURE:
<223> OTHER INFORMATION: Artificial sequence from RNA display

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met His Trp Val Arg Gln Ala Pro Gly Lys Gly Leu Glu Trp Val
        35                  40                  45

Ser Ala Ile Ser Gly Asn Gly Gly Ser Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Phe Arg Lys Val His Gly Phe Asp Val Trp Gly Gln
            100                 105                 110

Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Artificial sequence from RNA display

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Ala Thr Phe Pro Leu
                85                  90                  95

Thr Phe Gly Gln Gly Thr Lys Val Glu Ile Lys
            100                 105
```

<210> SEQ ID NO 3
<211> LENGTH: 119
<212> TYPE: PRT
<213> ORGANISM: Artificial Sequence
<220> FEATURE:
<223> OTHER INFORMATION: Artificial sequence from RNA display

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Gly Ser Gly Gly Ser Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Trp Ser Lys Trp Gly Phe Asp Val Trp Gly Gln Gly
            100                 105                 110

Thr Leu Val Thr Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: Artificial sequence from RNA display

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Phe Pro Tyr
                85                  90                  95

Thr Phe Gly Gln Gly Thr Lys Val Glu Ile Lys
            100                 105